United States Patent
Sharma

(10) Patent No.: US 11,000,607 B2
(45) Date of Patent: May 11, 2021

(54) METHODS AND SYSTEMS FOR THE STERILIZATION OF ENDOSCOPES

(71) Applicant: Virender K. Sharma, Paradise Valley, AZ (US)

(72) Inventor: Virender K. Sharma, Paradise Valley, AZ (US)

( * ) Notice: Subject to any disclaimer, the term of this patent is extended or adjusted under 35 U.S.C. 154(b) by 0 days.

(21) Appl. No.: 16/420,472

(22) Filed: May 23, 2019

(65) Prior Publication Data

US 2020/0147246 A1    May 14, 2020

Related U.S. Application Data

(62) Division of application No. 15/155,029, filed on May 15, 2016, now Pat. No. 10,350,318.

(60) Provisional application No. 62/162,629, filed on May 15, 2015.

(51) Int. Cl.
| | |
|---|---|
| *A61L 2/07* | (2006.01) |
| *A61B 1/12* | (2006.01) |
| *A61L 2/24* | (2006.01) |
| *A61L 2/28* | (2006.01) |
| A61B 90/70 | (2016.01) |

(52) U.S. Cl.
CPC ............... *A61L 2/07* (2013.01); *A61B 1/123* (2013.01); *A61B 1/125* (2013.01); *A61L 2/24* (2013.01); *A61L 2/28* (2013.01); *A61B 2090/701* (2016.02); *A61L 2202/14* (2013.01); *A61L 2202/24* (2013.01)

(58) Field of Classification Search
CPC ... A61L 2/07; A61L 2/24; A61B 1/123; A61B 1/125
See application file for complete search history.

(56) References Cited

U.S. PATENT DOCUMENTS

| | | |
|---|---|---|
| 4,380,530 A | 4/1983 | Kaye |
| 5,534,221 A | 7/1996 | Hillebrenner et al. |
| 6,187,266 B1 | 2/2001 | Lin |
| | (Continued) | |

FOREIGN PATENT DOCUMENTS

| | | |
|---|---|---|
| CN | 201085795 | 7/2008 |
| WO | 2012091521 A2 | 7/2012 |
| WO | 2016187080 A1 | 11/2016 |

OTHER PUBLICATIONS

International Search Report for PCT/US2016/032610, dated Sep. 22, 2016.

*Primary Examiner* — Kevin Joyner

(74) *Attorney, Agent, or Firm* — Novel IP

(57) ABSTRACT

A method and device for high-pressure, high-temperature steam sterilization of endoscopes includes pressure resistant fittings to attach a steam generator to the ports of an endoscope. The method and device allows for high-pressure, high-temperature steam to circulate throughout the endoscope, exposing various surfaces to steam for sterilization. The method and device also allows for high-pressure, high-temperature steam to circulate selectively through the channels of the endoscope, selectively sterilizing the channels and allowing for use of this method with current high-level disinfection methods. The method and device also allows for movement of the scope elevator channel during the sterilization process, allowing for steam to reach the crevices around the elevator and other moving parts of an endoscope.

20 Claims, 32 Drawing Sheets

(56) References Cited

U.S. PATENT DOCUMENTS

| | | |
|---|---|---|
| 2001/0033806 A1 | 10/2001 | Stanley |
| 2004/0091389 A1 | 5/2004 | Malkin |
| 2005/0025686 A1 | 2/2005 | Sargent |
| 2005/0065402 A1* | 3/2005 | Moriyama ................ A61L 2/07 600/133 |
| 2005/0148819 A1 | 7/2005 | Noguchi |
| 2006/0263245 A1 | 11/2006 | Watanabe |
| 2013/0195717 A1 | 8/2013 | Fehr |

* cited by examiner

METHODS AND SYSTEMS FOR THE STERILIZATION OF ENDOSCOPES

CROSS-REFERENCE

The present application is a division application of U.S. patent application Ser. No. 15/155,029, entitled "Method and System for Steam Sterilization of Endoscopes" and filed on May 15, 2016, which relies on U.S. Provisional Patent Application No. 62/162,629, of the same title and filed on May 15, 2015, for priority, both of which are herein incorporated by reference in their entirety.

FIELD

The present specification relates to apparatuses, systems, and methods for cleaning, disinfecting or sterilizing medical instruments and devices. More particularly, the present specification relates to systems and methods for sterilizing medical devices, such as catheters and endoscopes, using superheated steam, or any other suitable sterilizing agent.

BACKGROUND

According to the Centers for Disease Control and Prevention, approximately 46.5 million surgical procedures are performed each year in the United States. Of those, approximately 5 million comprise gastrointestinal endoscopies, considered a more invasive medical procedure. Following these endoscopies, disinfection and sterilization are essential for ensuring that the medical and surgical instruments do not transmit infectious pathogens to subsequent patients.

Cleaning is described as the removal of visible soil (e.g., organic and inorganic material) from objects and surfaces and normally is accomplished manually or mechanically using water with detergents or enzymatic products. Thorough cleaning is essential before high-level disinfection and sterilization because inorganic and organic materials that remain on the surfaces of instruments interfere with the effectiveness of these processes. Also, if soiled materials dry or bake onto the instruments, the removal process becomes more difficult and the disinfection or sterilization process less effective or ineffective. Surgical instruments are typically presoaked or rinsed to prevent drying of blood and to soften or remove blood from the instruments.

Cleaning is done manually in use areas without mechanical units (e.g., ultrasonic cleaners or washer-disinfectors) or for fragile or difficult-to-clean instruments. With manual cleaning, the two essential components are friction and fluidics. Friction is accomplished, for example, by rubbing/scrubbing the soiled area with a brush. Fluidics (i.e., fluids under pressure) is used to remove soil and debris from internal channels after brushing and when the design does not allow passage of a brush through a channel. When a washer-disinfector is used, care is taken in loading instruments. For example, hinged instruments are opened fully to allow adequate contact with the detergent solution, stacking of instruments in washers is avoided, and instruments are disassembled as much as possible.

The most common types of mechanical or automatic cleaners are ultrasonic cleaners, washer-decontaminators, washer-disinfectors, and washer-sterilizers. Ultrasonic cleaning removes soil by cavitation and implosion in which waves of acoustic energy are propagated in aqueous solutions to disrupt the bonds that hold particulate matter to surfaces.

Disinfection describes a process that eliminates many or all pathogenic microorganisms, except bacterial spores, on inanimate objects. Disinfection is usually performed using liquid chemicals or wet pasteurization. High-level disinfection traditionally is defined as complete elimination of all microorganisms in or on an instrument, except for small numbers of bacterial spores. The Food and Drug Administration (FDA) definition of high-level disinfection is a sterilant used for a shorter contact time to achieve a 6-log 10 kill of an appropriate *Mycobacterium* species. Cleaning followed by high-level disinfection should eliminate enough pathogens to prevent transmission of infection.

Laparoscopes and arthroscopes in the United States sometimes undergo only high-level disinfection between patients. As with flexible endoscopes, these devices can be difficult to clean and high-level disinfect or sterilize because of intricate device design (e.g., long narrow lumens, hinges). Meticulous cleaning must precede any high-level disinfection or sterilization process.

Sterilization describes a process that destroys or eliminates all forms of microbial life and is carried out in health-care facilities by physical or chemical methods. Steam under pressure, dry heat, ethylene oxide (EtO) gas, hydrogen peroxide gas plasma, and liquid chemicals are the principal sterilizing agents used in health-care facilities.

Factors that affect the efficacy of both disinfection and sterilization include prior cleaning of the object, organic and inorganic load present, type and level of microbial contamination, concentration of and exposure time to the germicide, physical nature of the object (e.g., crevices, hinges, and lumens), presence of biofilms, temperature and pH of the disinfection process, and in some cases, relative humidity of the sterilization process.

Decontamination removes pathogenic microorganisms from objects so they are safe to handle, use, or discard.

Rinsing endoscopes and flushing endoscope channels with sterile water, filtered water, or tap water will prevent adverse effects associated with disinfectant retained in the endoscope (e.g., disinfectant-induced colitis). Items can be rinsed and flushed using sterile water after high-level disinfection to prevent contamination with organisms in tap water, such as nontuberculous mycobacteria, *Legionella*, or gram-negative bacilli such as *Pseudomonas*. Alternatively, a tap water or filtered water (0.2 m filter) rinse should be followed by an alcohol rinse and forced air drying. Forced-air drying markedly reduces bacterial contamination of stored endoscopes, most likely by removing the wet environment favorable for bacterial growth. After rinsing, items should be dried and stored (e.g., packaged) in a manner that protects them from recontamination.

Physicians use endoscopes to diagnose and treat numerous medical disorders. Even though endoscopes represent a valuable diagnostic and therapeutic tool in modern medicine and the incidence of infection associated with their use reportedly is very low (about 1 in 1.8 million procedures), more healthcare-associated outbreaks have been linked to contaminated endoscopes than to any other medical device. To prevent the spread of health-care-associated infections, all heat-sensitive endoscopes (e.g., gastrointestinal endoscopes, bronchoscopes, nasopharyngoscopes) must be properly cleaned and, at a minimum, subjected to high-level disinfection after each use. High-level disinfection can be expected to destroy all microorganisms, although when high numbers of bacterial spores are present, a few spores might survive.

Because of the types of body cavities they enter, flexible endoscopes acquire high levels of microbial contamination (bioburden) during each use. For example, the bioburden found on flexible gastrointestinal endoscopes after use has ranged from $10^5$ colony forming units (CFU)/mL to $10^{10}$ CFU/mL, with the highest levels found in the suction channels. The average load on bronchoscopes before cleaning was $6.4 \times 10^4$ CFU/ml. Cleaning reduces the level of microbial contamination by 4-6 $\log_{10}$. Using human immunovirus (HIV)-contaminated endoscopes, several investigators have shown that cleaning completely eliminates the microbial contamination on the scopes. Similarly, other investigators found that EtO sterilization or soaking in 2% glutaraldehyde for 20 minutes was effective only when the device first was properly cleaned.

The FDA maintains a list of cleared liquid chemical sterilants and high-level disinfectants that can be used to reprocess heat-sensitive medical devices, such as flexible endoscopes. At this time, the FDA-cleared and marketed formulations include: ≥2.4% glutaraldehyde, 0.55% ortho-phthalaldehyde (OPA), 0.95% glutaraldehyde with 1.64% phenol/phenate, 7.35% hydrogen peroxide with 0.23% peracetic acid, 1.0% hydrogen peroxide with 0.08% peracetic acid, and 7.5% hydrogen peroxide. These products have excellent antimicrobial activity; however, some oxidizing chemicals (e.g., 7.5% hydrogen peroxide and 1.0% hydrogen peroxide with 0.08% peracetic acid) reportedly have caused cosmetic and functional damage to endoscopes. EtO sterilization of flexible endoscopes is infrequent because it requires a lengthy processing and aeration time (e.g., 12 hours) and is a potential hazard to staff and patients. The two products most commonly used for reprocessing endoscopes in the United States are glutaraldehyde and an automated, liquid chemical sterilization process that uses peracetic acid. The American Society for Gastrointestinal Endoscopy (ASGE) recommends glutaraldehyde solutions that do not contain surfactants because the soapy residues of surfactants are difficult to remove during rinsing. Ortho-phthalaldehyde has begun to replace glutaraldehyde in many health-care facilities because it has several potential advantages over glutaraldehyde. Ortho-phthalaldehyde is not known to irritate the eyes and nasal passages, does not require activation or exposure monitoring, and has a 12-minute high-level disinfection claim in the United States. Disinfectants that are not FDA-cleared and should not be used for reprocessing endoscopes include iodophors, chlorine solutions, alcohols, quaternary ammonium compounds, and phenolics. These solutions might still be in use outside the United States, but their use is discouraged because of lack of proven efficacy against all microorganisms or materials incompatibility.

Flexible endoscopes are particularly difficult to disinfect and easy to damage because of their intricate design and delicate materials. Meticulous cleaning must precede any sterilization or high-level disinfection of these instruments. Failure to perform good cleaning can result in sterilization or disinfection failure and outbreaks of infection can occur. Several studies have demonstrated the importance of cleaning in experimental studies with the duck hepatitis B virus (HBV), HIV, and *Helicobacter pylori*.

An examination of health-care-associated infections related only to endoscopes through July 1992 found 281 infections transmitted by gastrointestinal endoscopy and 96 transmitted by bronchoscopy. The clinical spectrum ranged from asymptomatic colonization to death. *Salmonella* species and *Pseudomonas aeruginosa* repeatedly were identified as causative agents of infections transmitted by gastrointestinal endoscopy, and *M. tuberculosis*, atypical mycobacteria, and *P. aeruginosa* were the most common causes of infections transmitted by bronchoscopy. Major reasons for transmission were inadequate cleaning, improper selection of a disinfecting agent, failure to follow recommended cleaning and disinfection procedures, and flaws in endoscope design or automated endoscope reprocessors. Failure to follow established guidelines has continued to result in infections associated with gastrointestinal endoscopes and bronchoscopes. One multistate investigation found that 23.9% of the bacterial cultures from the internal channels of 71 gastrointestinal endoscopes grew >100,000 colonies of bacteria after completion of all disinfection and sterilization procedures and before use on the next patient.

Automated endoscope reprocessors (AER) offer several advantages over manual reprocessing. AERs automate and standardize several important reprocessing steps, reduce the likelihood that an essential reprocessing step will be skipped, and reduce personnel exposure to high-level disinfectants or chemical sterilants. Failure of AERs has been linked to outbreaks of infections or colonization, and the AER water filtration system might not be able to reliably provide "sterile" or bacteria-free rinse water. Establishment of correct connectors between the AER and the device is critical to ensure complete flow of disinfectants and rinse water. In addition, some endoscopes, such as the duodenoscopes (e.g., for endoscopic retrograde cholangiopancreatography [ERCP]), contain features (e.g., elevator-wire channel) that require a flushing pressure that is not achieved by most AERs and must be reprocessed manually using a 2- to 5-mL syringe, until new duodenoscopes equipped with a wider elevator-channel that AERs can reliably reprocess become available. Outbreaks involving removable endoscope parts, such as suction valves and endoscopic accessories designed to be inserted through flexible endoscopes, such as biopsy forceps, emphasize the importance of cleaning to remove all foreign matter before high-level disinfection or sterilization. Some types of valves are now available as single-use, disposable products (e.g., bronchoscope valves) or steam sterilizable products (e.g., gastrointestinal endoscope valves).

AERs need further development and redesign, as do endoscopes, so that they do not represent a potential source of infectious agents. Endoscopes employing disposable components (e.g., protective barrier devices or sheaths) might provide an alternative to conventional liquid chemical high-level disinfection/sterilization. Another new technology is a swallowable camera-in-a-capsule that travels through the digestive tract and transmits color pictures of the small intestine to a receiver worn outside the body. This capsule currently does not replace colonoscopies.

In general, endoscope disinfection or sterilization with a liquid chemical sterilant involves five steps after leak testing:

1. Clean: mechanically clean internal and external surfaces, including brushing internal channels and flushing each internal channel with water and a detergent or enzymatic cleaners (leak testing is recommended for endoscopes before immersion).
2. Disinfect: immerse endoscope in high-level disinfectant (or chemical sterilant) and perfuse (eliminates air pockets and ensures contact of the germicide with the internal channels) disinfectant into all accessible channels, such as the suction/biopsy channel and air/water channel and expose for a time recommended for specific products.
3. Rinse: rinse the endoscope and all channels with sterile water, filtered water (commonly used with AERs) or tap water (i.e., high-quality potable water that meets federal clean water standards at the point of use).

4. Dry: rinse the insertion tube and inner channels with alcohol, and dry with forced air after disinfection and before storage.
5. Store: store the endoscope in a way that prevents recontamination and promotes drying.

Methicillin-resistant *Staphylococcus aureus* (MRSA) and vancomycin-resistant *Enterococcus* (VRE) are important health-care-associated agents. Some antiseptics and disinfectants have been known to be somewhat less inhibitory to *Staphylococcus aureus* strains that contain a plasmid-carrying gene encoding resistance to the antibiotic gentamicin. For example, gentamicin resistance has been shown to also encode reduced susceptibility to propamidine, quaternary ammonium compounds, and ethidium bromide, and MRSA strains have been found to be less susceptible than methicillin-sensitive *Staphylococcus aureus* (MSSA) strains to chlorhexidine, propamidine, and the quaternary ammonium compound cetrimide. In other studies, MRSA and MSSA strains have been equally sensitive to phenols and chlorhexidine, but MRSA strains were slightly more tolerant to quaternary ammonium compounds. Two gene families (qacCD [now referred to as smr] and qacAB) are involved in providing protection against agents that are components of disinfectant formulations such as quaternary ammonium compounds. Staphylococci have been proposed to evade destruction because the protein specified by the qacA determinant is a cytoplasmic-membrane-associated protein involved in an efflux system that actively reduces intracellular accumulation of toxicants, such as quaternary ammonium compounds, to intracellular targets.

A study that evaluated the efficacy of selected cleaning methods (e.g., quaternary ammonium cation [QUAT]-sprayed cloth, and QUAT-immersed cloth) for eliminating VRE found that currently used disinfection processes most likely are highly effective in eliminating VRE. However, surface disinfection must involve contact with all contaminated surfaces.

Organic matter in the form of serum, blood, pus, fecal, or lubricant material can interfere with the antimicrobial activity of disinfectants in at least two ways. Most commonly, interference occurs by a chemical reaction between the germicide and the organic matter resulting in a complex that is less germicidal or nongermicidal, leaving less of the active germicide available for attacking microorganisms. Chlorine and iodine disinfectants, in particular, are prone to such interaction. Alternatively, organic material can protect microorganisms from attack by acting as a physical barrier.

All lumens and channels of endoscopic instruments must contact the disinfectant. Air pockets interfere with the disinfection process, and items that float on the disinfectant will not be disinfected. The disinfectant must be introduced reliably into the internal channels of the device. The exact times for disinfecting medical items are somewhat elusive because of the effect of the aforementioned factors on disinfection efficacy. Certain contact times have proved reliable, but, in general, longer contact times are more effective than shorter contact times.

Microorganisms may be protected from disinfectants by the production of thick masses of cells and extracellular materials, or biofilms.

Of all the methods available for sterilization, moist heat in the form of saturated steam under pressure is the most widely used and the most dependable. Steam sterilization is nontoxic, inexpensive, rapidly microbicidal, sporicidal, and rapidly heats and penetrates fabrics. Like all sterilization processes, steam sterilization has some deleterious effects on some materials, including corrosion and combustion of lubricants associated with dental handpieces, reduction in ability to transmit light associated with laryngoscopes, and increased hardening time (5.6 fold) with plaster-cast.

The basic principle of steam sterilization, as accomplished in an autoclave, is to expose each item to direct steam contact at the required temperature and pressure for the specified time. Thus, there are four parameters of steam sterilization: steam, pressure, temperature, and time. The ideal steam for sterilization is dry saturated steam and entrained water (dryness fraction ≥97%). Pressure serves as a means to obtain the high temperatures necessary to quickly kill microorganisms. Specific temperatures must be obtained to ensure the microbicidal activity. The two common steam-sterilizing temperatures are 121° C. (250° F.) and 132° C. (270° F.). These temperatures (and other high temperatures) must be maintained for a minimal time to kill microorganisms. Recognized minimum exposure periods for sterilization of wrapped healthcare supplies are 30 minutes at 121° C. (250° F.) in a gravity displacement sterilizer or 4 minutes at 132° C. (270° C.) in a prevacuum sterilizer. At constant temperatures, sterilization times vary depending on the type of item (e.g., metal versus rubber, plastic, items with lumens), whether the item is wrapped or unwrapped, and the sterilizer type.

The two basic types of steam sterilizers (autoclaves) are the gravity displacement autoclave and the high-speed prevacuum sterilizer.

Another design in steam sterilization is a steam flush-pressure pulsing process, which removes air rapidly by repeatedly alternating a steam flush and a pressure pulse above atmospheric pressure. Air is rapidly removed from the load as with the prevacuum sterilizer, but air leaks do not affect this process because the steam in the sterilizing chamber is always above atmospheric pressure. Typical sterilization temperatures and times are 132° C. to 135° C. with 3 to 4 minutes exposure time for porous loads and instruments.

Moist heat destroys microorganisms by the irreversible coagulation and denaturation of enzymes and structural proteins. In support of this fact, it has been found that the presence of moisture significantly affects the coagulation temperature of proteins and the temperature at which microorganisms are destroyed.

Steam sterilization should be used whenever possible on all critical and semicritical items that are heat and moisture resistant (e.g., steam sterilizable respiratory therapy and anesthesia equipment), even when not essential to prevent pathogen transmission. Steam sterilizers also are used in healthcare facilities to decontaminate microbiological waste and sharps containers but additional exposure time is required in the gravity displacement sterilizer for these items.

"Flash" steam sterilization was originally defined by Underwood and Perkins as sterilization of an unwrapped object at 132° C. for 3 minutes at 27-28 lbs. of pressure in a gravity displacement sterilizer.

Hydrogen peroxide is another agent used in disinfection and sterilization. Published reports ascribe good germicidal activity to hydrogen peroxide and attest to its bactericidal, virucidal, sporicidal, and fungicidal properties. Hydrogen peroxide works by producing destructive hydroxyl free radicals that can attack membrane lipids, DNA, and other essential cell components. Catalase, produced by aerobic organisms and facultative anaerobes that possess cytochrome systems, can protect cells from metabolically produced hydrogen peroxide by degrading hydrogen peroxide to water and oxygen. This defense is overwhelmed by the concentrations used for disinfection. Concentrations of hydrogen peroxide from 6% to 25% show promise as chemical sterilants. The product marketed as a sterilant is a premixed, ready-to-use chemical that contains 7.5% hydrogen peroxide and 0.85% phosphoric acid (to maintain a low pH). When the effectiveness of 7.5% hydrogen peroxide at 10 minutes was compared with 2% alkaline glutaraldehyde at 20 minutes in manual disinfection of endoscopes, no significant difference in germicidal activity was observed. A new, rapid-acting 13.4% hydrogen peroxide formulation (that is not yet FDA-cleared) has demonstrated sporicidal, mycobactericidal, fungicidal, and virucidal efficacy. Manufacturer data demonstrate that this solution sterilizes in 30 minutes and provides high-level disinfection in 5 minutes.

SUMMARY

The present specification discloses a method of disinfecting or sterilizing an endoscope where the endoscope has an external surface and a lumen, said method comprising the steps of: attaching a pressure resistance fitting to the scope tip or one of the openings of the lumen; and delivering super-heated steam through the pressure fitting.

Optionally, the method further includes the step of attaching a suction mechanism to one of the other openings of the lumen and suctioning the super-heated steam.

The delivery of superheated steam and the rate of suction may be controlled by a microprocessor.

Optionally, at least one temperature or pressure sensor is housed in a path of the superheated steam wherein said method further comprises the step of using data from said at least one sensor to control the rate of flow of superheated steam or the rate of suction.

Optionally, said microprocessor includes a user interface to input data from an operator and provide progress information back to the operator.

The present specification also discloses an apparatus for disinfecting or sterilizing an endoscope, comprising: at least one pressure resistant compression fitting designed to be operably attached to one opening of an endoscope; a steam generator capable of generating super-heated steam and attached to said at least one pressure resistant compression fitting via a length of tubing; at least one pressure resistant vacuum suction fitting designed to be operably attached to another opening of an endoscope at one end and attached to a vacuum suction at the other end; and a microprocessor operably attached to the steam generator and vacuum pump to control the rate of delivery of steam and rate of suction.

Optionally, the apparatus further comprises additional steam delivery ports for delivery of steam into one of the other openings of the endoscope.

Optionally, the apparatus further comprises additional suction ports for suction of steam from one of the other openings of the endoscope.

Optionally, the apparatus further comprises sensors to measure at least one of a plurality of parameters of the steam and input measured data into the microprocessor to control the delivery of steam or rate of suction or both.

Optionally, the microprocessor further comprises a user interface to input operational data or to monitor the progress of disinfection or sterilization.

The present specification also discloses a method of disinfecting or sterilizing an endoscope where the endoscope has an external surface and a lumen, said method comprising the steps of: placing the endoscope in a thermally insulating casing designed to house the endoscope; attaching a pressure resistance fitting to the scope tip or one of the openings of the lumen; delivering super-heated steam through the pressure fitting to fill the endoscope channels; and allowing the steam to escape from one of the other openings in the endoscope and into a space between the endoscope and the casing.

Optionally, the method further comprises the steps of attaching a suction mechanism to the casing and suctioning the super-heated steam from around the endoscope to maintain the desired pressure and temperature.

The delivery of superheated steam and the rate of suction may be controlled by a microprocessor.

Optionally, at least one temperature or pressure sensor is housed in a path of the superheated steam and said method further comprises the step of using data from said at least one sensor to control the rate of flow of superheated steam or the rate of suction.

Optionally, said microprocessor includes a user interface to input data from an operator and provide progress information back to the operator.

The present specification also discloses an apparatus for disinfecting or sterilizing an endoscope, comprising: a thermally insulating casing with at least one pressure resistant compression fitting designed to be operably attached to one opening of an endoscope; a steam generator capable of generating and delivering super-heated steam and attached to said pressure resistant compressing fitting; at least one vacuum suction port operably attached to the casing at one end and attached to a vacuum suction at the other end to provide suction; and a microprocessor operably attached to the steam generator and vacuum pump to control the rate of delivery of steam and rate of suction.

Optionally, the apparatus further comprises additional steam delivery ports for delivery of steam into one of the other openings of the endoscope.

Optionally, the apparatus further comprises additional suction ports for the suction of steam from one of the other openings of the endoscope.

Optionally, the apparatus further comprises at least one sensor to measure any one of a plurality of parameters of the steam and input measured data into the microprocessor to control the delivery of steam or rate of suction or both.

Optionally, said microprocessor includes a user interface to input operational data or to monitor the progress of disinfection or sterilization.

The present specification also discloses an apparatus for disinfecting or sterilizing an endoscope, comprising: at least two chambers separated by a removable separating component; a space for placing an endoscope wherein a first portion of said endoscope comprising at least one first endoscope port is positioned in a first chamber of said at least two chambers and a second portion of said endoscope comprising at least one second endoscope port is positioned in a second chamber of said at least two chambers; at least one first opening providing fluid communication between said first chamber and an outside area of said apparatus; and at least one second opening providing fluid communication between said second chamber and an outside area of said apparatus; wherein a disinfecting or sterilizing agent is introduced under pressure through said first or second opening and into said first or second chamber and wherein a pressure difference between said first chamber and said second chamber causes said disinfecting or sterilizing agent to enter said endoscope through said first endoscope port or said second endoscope port, pass through one or more endoscope channels of said endoscope, exit said endoscope through said first endoscope port or said second endoscope port not comprising the endoscope port through which said disinfecting or sterilizing agent entered said endoscope, and exit said apparatus through said first or second opening not comprising the opening through which the disinfecting or sterilizing agent entered said apparatus.

The aforementioned and other embodiments of the present invention shall be described in greater depth in the drawings and detailed description provided below.

BRIEF DESCRIPTION OF THE DRAWINGS

These and other features and advantages of the present invention will be further appreciated, as they become better understood by reference to the detailed description when considered in connection with the accompanying drawings, wherein.

DETAILED DESCRIPTION

Figure 1A:
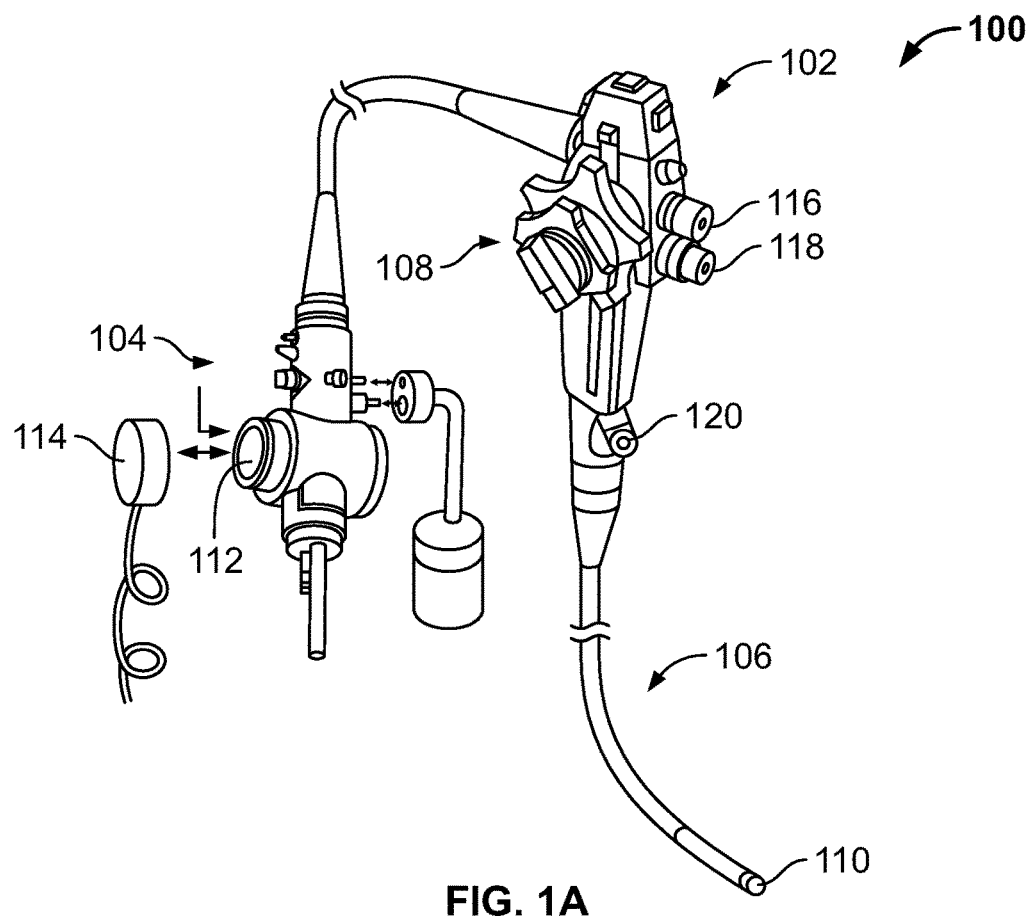
FIG. 1A is an illustration of an endoscope, depicting a plurality of ports.

The present specification discloses apparatuses and methods for reprocessing, disinfecting, or sterilizing medical equipment, such as endoscopes, using steam or other sterilizing or disinfecting agents known in the art. The devices are sterilized by attaching a mechanism having a pressure resistant, compression fitting to the tip of an endoscope wherein the mechanism is configured to deliver superheated (SH) steam or another sterilizing agent. Additional pressure resistant fittings are attached to the openings in the various channels of the endoscope and a vacuum pump is attached to each channel, thus creating a closed system for the circulation of the sterilizing or disinfecting agent. Optional pressure and temperature sensors are disposed in various fittings to monitor the pressure and the temperature of the closed system. Optional pressure regulated valves are disposed in various fittings to open when a certain pressure is reached.

"Treat," "treatment," and variations thereof refer to any reduction in the extent, frequency, or severity of one or more symptoms or signs associated with a condition.

"Duration" and variations thereof refer to the time course of a prescribed treatment, from initiation to conclusion, whether the treatment is concluded because the condition is resolved or the treatment is suspended for any reason. Over the duration of treatment, a plurality of treatment periods may be prescribed during which one or more prescribed stimuli are administered to the subject.

"Period" refers to the time over which a "dose" of stimulation is administered to a subject as part of the prescribed treatment plan.

The term "and/or" means one or all of the listed elements or a combination of any two or more of the listed elements.

The terms "comprises" and variations thereof do not have a limiting meaning where these terms appear in the description and claims.

Unless otherwise specified, "a," "an," "the," "one or more," and "at least one" are used interchangeably and mean one or more than one.

For any method disclosed herein that includes discrete steps, the steps may be conducted in any feasible order. And, as appropriate, any combination of two or more steps may be conducted simultaneously.

Also herein, the recitations of numerical ranges by endpoints include all numbers subsumed within that range (e.g., 1 to 5 includes 1, 1.5, 2, 2.75, 3, 3.80, 4, 5, etc.). Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present specification. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the specification are approximations, the numerical values set forth in the specific examples are reported as precisely as possible. All numerical values, however, inherently contain a range necessarily resulting from the standard deviation found in their respective testing measurements.

The present invention is directed towards multiple embodiments. The following disclosure is provided in order to enable a person having ordinary skill in the art to practice the invention. Language used in this specification should not be interpreted as a general disavowal of any one specific embodiment or used to limit the claims beyond the meaning of the terms used therein. The general principles defined herein may be applied to other embodiments and applications without departing from the spirit and scope of the invention. Also, the terminology and phraseology used is for the purpose of describing exemplary embodiments and should not be considered limiting. Thus, the present invention is to be accorded the widest scope encompassing numerous alternatives, modifications and equivalents consistent with the principles and features disclosed. For purpose of clarity, details relating to technical material that is known in the technical fields related to the invention have not been described in detail so as not to unnecessarily obscure the present invention.

It should be noted herein that any feature or component described in association with a specific embodiment may be used and implemented with any other embodiment unless clearly indicated otherwise.

In one embodiment, an apparatus for reprocessing, disinfecting, or sterilizing medical equipment, such as endoscopes, comprises a mechanism, such as a steam generator, having a pressure resistant, compression fitting which is attached to the tip of an endoscope and configured to deliver superheated (SH) steam or hydrogen peroxide or another sterilizing agent. Tubing connects the compression fitting to a steam generator. Additional pressure resistant fittings are attached to the openings in the various channels of the endoscope. An attachment to a vacuum pump is included per channel, thus creating a closed system for the circulation of steam or a sterilizing agent. In some embodiments, optional pressure and temperature sensors are disposed in various fittings to monitor the pressure and the temperature of the closed system. In some embodiments, optional pressure regulated valves are disposed in various fittings to open when a certain pressure is reached.

Super-heated (SH) steam at a desired temperature and pressure is delivered through the compression fitting at the endoscope tip. The steam is pushed into various channels, pressurizing these channels. In one embodiment, once the desired pressure is reached, pressure regulated valves open, allowing the steam to escape for circulation of the steam at the desired pressure and temperature through the channel. The SH steam is circulated for a desired duration to achieve the desired therapeutic effect. In some embodiments, optional mechanisms to suction away the steam to prevent operator injury are disposed in the system. Optionally, in some embodiments, the whole system and the endoscope are housed in a thermally insulating casing to prevent the escape of steam and injury to the operator. In some embodiments, the casing further houses optional temperature and pressure sensors to monitor the progress of sterilization. In some embodiments, optional temperature and pressure sensors are disposed in various fittings to monitor the sterilization process. In various embodiments, the delivery of SH steam is controlled by a microprocessor and modified by input from various sensors. In some embodiments, the microprocessor has a user interface for users to input various parameters for adequate sterilization.

In one embodiment, the operator can manipulate the elevator control lever to move the elevator of a duodenoscope, allowing for SH steam to enter various crevices around the elevator. In another embodiment, a mechanical mechanism is used to manipulate the elevator lever while the steam is being circulated.

In another embodiment the sterilizing agent is hydrogen peroxide or ionized plasma gas. In some embodiments the sterilization process can be combined with other sterilizing agents such as UV radiation or ethylene oxide sterilization or other sterilization agents known in the field.

In another embodiment, the pressure resistant fittings attached to the various channel openings are attached to a vacuum controlled by a microprocessor. As the delivery of SH steam starts, the vacuum starts suctioning the air in the various channels, allowing for steam to flow throughout the channel. As the temperature of the suctioned air approaches 100° C., the vacuum shuts down, creating a closed system while the SH steam is continually being delivered. Both the temperature and the pressure in the scope channels rise and, when the desired temperature or pressure value is reached, the vacuum restarts, circulating the superheated steam through the endoscope channels. The delivery of SH steam and the rate of vacuum are matched by the microprocessor to maintain a steady state temperature and pressure for a desired duration, following which the delivery of SH steam ceases and the channels are deemed to be sterilized.

In various embodiments, the pressure in the system is continually monitored and a certain change in the pressure may signal a blockage or a leak modifying or shutting down the flow of SH steam.

In one embodiment, the sterilization system includes a thermally insulated casing and the vacuum mechanism is part of the casing. In this embodiment, the SH steam is delivered at the tip through the compression fitting and it pushes the air out of the channel into the space between the endoscope and the casing. Pressure and temperature sensors are disposed in the casing. As the temperature or pressure reaches a predetermined value, the vacuum starts suctioning, circulating the SH steam in and around the endoscope. The delivery of SH steam and rate of vacuum suctioned are matched to maintain a steady state temperature and pressure for a desired duration to achieve the desired level of disinfection or sterilization.

In another embodiment, the sterilization system includes a thermally insulated casing and the SH steam delivery mechanism is part of the casing. In this embodiment, the SH steam is delivered from the casing into the space around the endoscope. The vacuum suction tubing is attached to at least one opening of each channel. Pressure and temperature sensors are disposed in the casing. At a predetermined time from the start of delivery of SH steam, the vacuum starts suctioning the air out of the channels, allowing for circulation of the SH steam in through the scope channel and around the endoscope. Alternatively, as the temperature or pressure reaches a predetermined value, the vacuum starts suctioning from the channel opening, thus circulating the SH steam in and around the endoscope. The delivery of SH steam and rate of vacuum suctioned are matched to maintain a steady state temperature and pressure for a desired duration to achieve the desired level of disinfection or sterilization. The input from various temperature and pressure sensors is used to determine the rate and flow of SH steam and the rate of vacuum suction.

In another embodiment, the steam is forced through the channels of an endoscope through a compression fitting attached to the tip of the endoscope. Additional pressure resistant fittings are applied to the other openings of the channels in the endoscope. At least one fitting per channel has a pressure relief valve that opens at a pressure lower than the sterilization pressure. As the steam is pumped into the scope channel, the pressure rises in the channel, opening one or more of the relief valves and allowing the steam to escape out of the scope channel into the space around the endoscope, circulating the steam in and around the endoscope. The steam is continually pumped until the desired pressures and temperatures are reached and are maintained for the desired duration to achieve the desired level of disinfection or sterilization.

In one embodiment, the pressure resistant compression fitting at the tip is an inflatable cuff that can be inflated and deflated to achieve the desired level of circulation and disinfection or sterilization.

In various embodiments, additional sterilization or disinfection steps or agents known in the art can be combined to achieve the desired level of sterilization or disinfection. In various embodiments, the methods of sterilization or disinfection of the present specification are combined with manual cleaning or other methods of sterilization or disinfection. In some embodiments, additional sterilization agents can be combined with SH steam to achieve the desired level of disinfection or sterilization.

In some embodiments, mechanical levers are housed in the casing to mechanically move any moving parts, such as an elevator control lever in an endoscope, allowing for SH steam to enter into crevices around the lever and also to dislodge any debris.

In various embodiments, a thermally insulating, water-tight fitting is provided to cover and protect the electronic connectors of the endoscope from water or thermal damage.

In some embodiments, the present specification also discloses an endoscope which can withstand high-pressure, high-temperature disinfection. In one embodiment, the endoscope skin is made of a thermally resistant material. In various embodiments, the thermally resistant material is one of silicone, Teflon®, polyethylene terephthalate (PET), polypropylene, polybenzimidazole, or a thermoplastic polymer or any other material that can withstand temperatures >100° C. and ideally >150° C.

In another embodiment, an additional insulation layer, comprising a thermally resistant material, is positioned between the skin of the endoscope and the internal components of the endoscope to prevent thermal damage to the endoscope components, such as the electronics.

FIG. 1A illustrates an endoscope comprising a plurality of ports. Endoscope 100 comprises a handle portion 102 coupled with a connector portion 104 and an insertion tube 106, which is inserted into a patient's body cavity. The handle portion 102 comprises a plurality of knobs and buttons 108 which are used to control and maneuver the insertion tube 106 within the patient's body. The distal end of the insertion tube 106 comprises a bending section 110 which may be controlled via the handle 102. The bending section 110 ends in a tip portion comprising one or more cameras for capturing images/videos of the patient's internal organs. The connector 104 is used to connect the endoscope to a controller/computer (not shown in the figure) via a connection port 112 which may be covered by a cover cap 114 when not in use. The controller may be connected to one or more display screens for displaying the images/videos captured by the endoscope 100. Endoscope 100 also comprises a plurality of ports such as ports 116, 118, 120 for inserting biopsy instruments into the patient's body cavity via the insertion tube 106 and for delivery of air, water and providing suction.

Figure 1B:
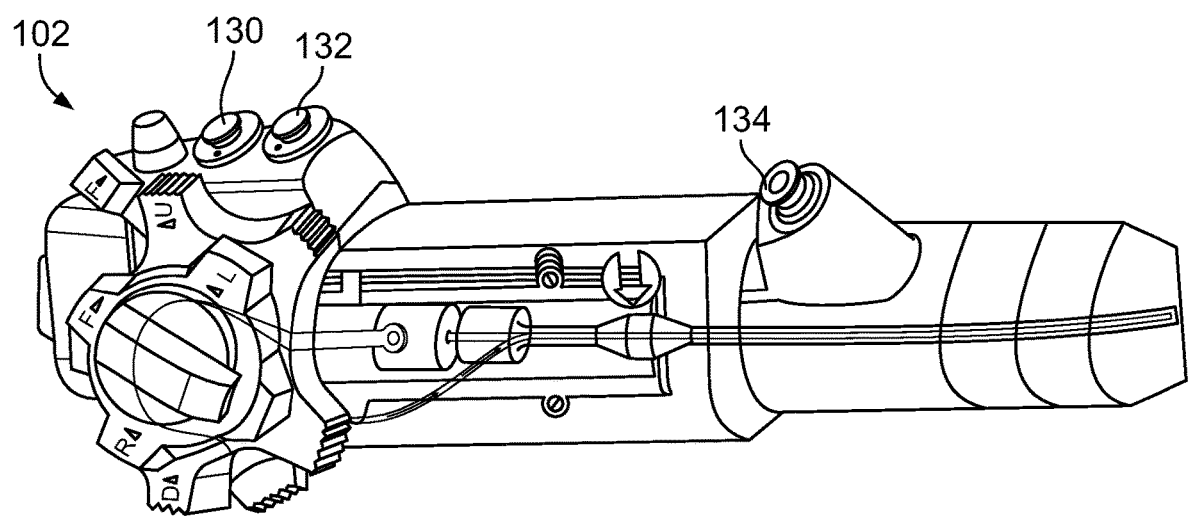
FIG. 1B is an illustration of an endoscope handle, depicting a plurality of ports.
Figure 1C:
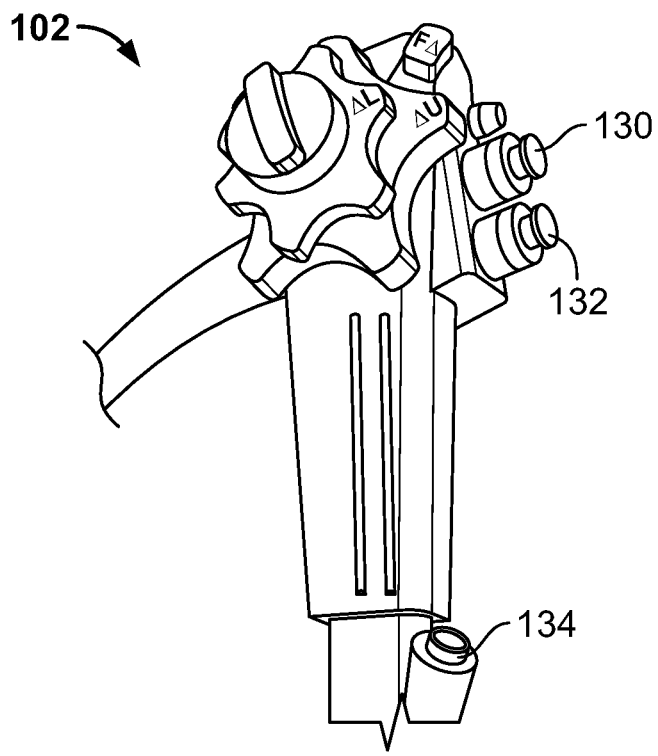
FIG. 1C is another illustration of an endoscope handle, depicting a plurality of ports.

FIG. 1B illustrates another view of an endoscope comprising a plurality of ports. FIG. 1C illustrates yet another view of an endoscope comprising a plurality of ports. Referring to FIGS. 1B and 1C simultaneously, handle 102 comprises a suction port 130 and an air/water port 132. A biopsy port 134 is provided for insertion of medical instruments into a patient's body cavity via the insertion tube of the endoscope.

Figure 1D:
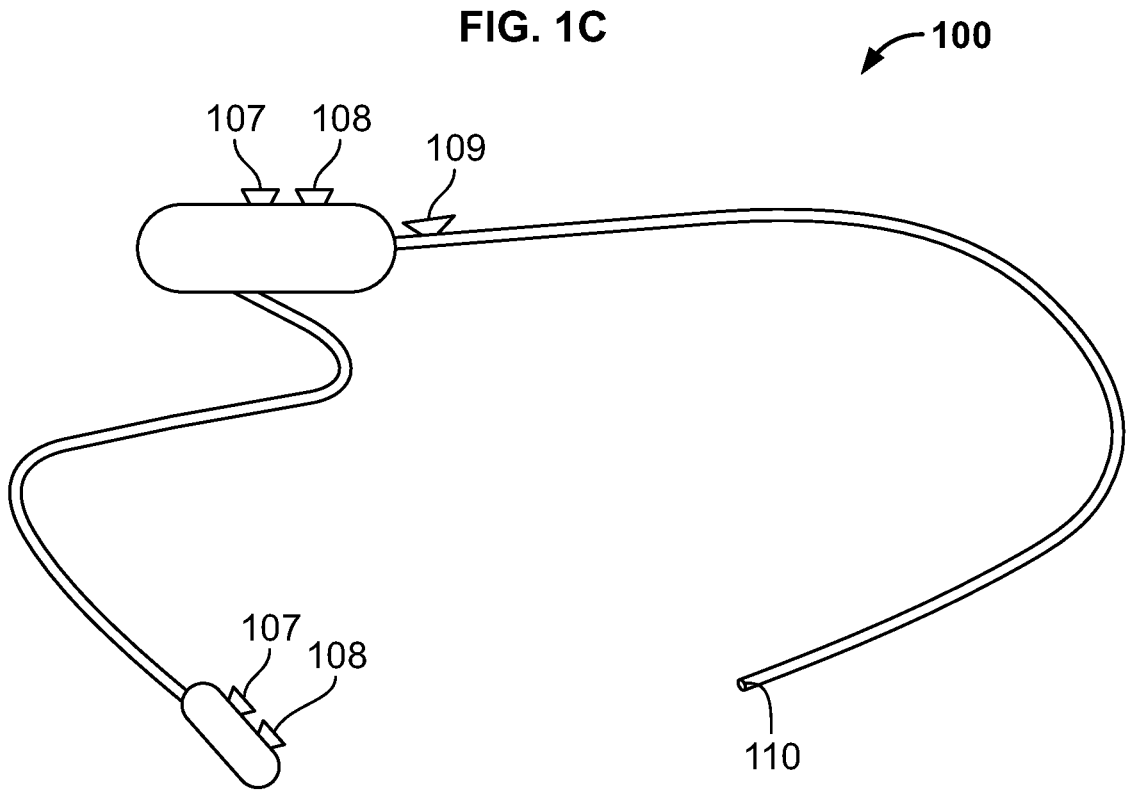
FIG. 1D is a block diagram of an endoscope, depicting a plurality of ports.

FIG. 1D is a block diagram of an endoscope 100, depicting a plurality of ports or openings 107, 108, 109. Ports 107 may be used to deliver water or air, ports 108 may be used for suction, and port 109 may be used for inserting biopsy tools. Each port 107, 108, 109 is in fluid communication with an opening at the distal tip 110 of the endoscope 100 via channels within the endoscope 100.

Figure 2:
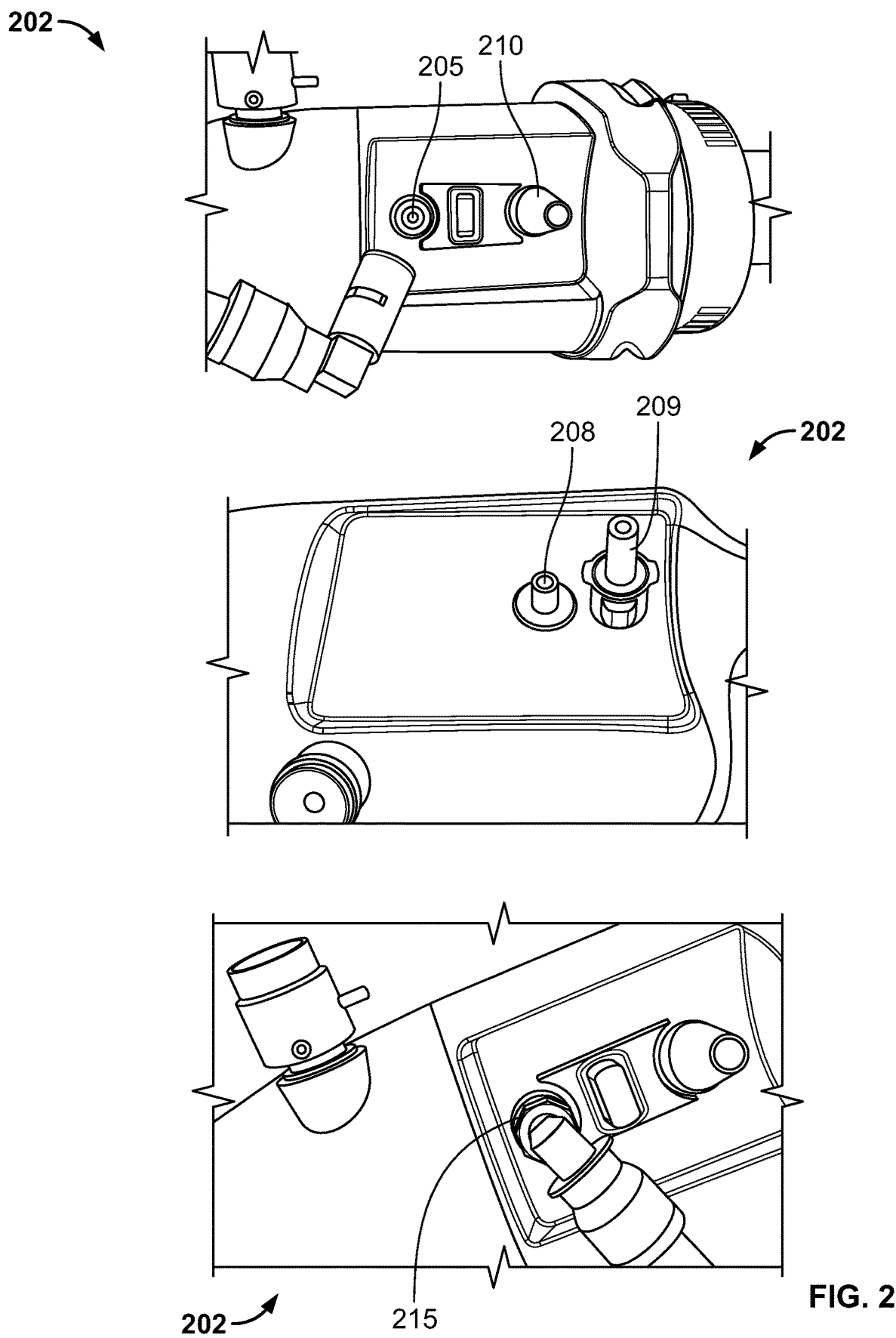
FIG. 2 is a close-up illustration of a plurality of ports on an endoscope.
Figure 3:
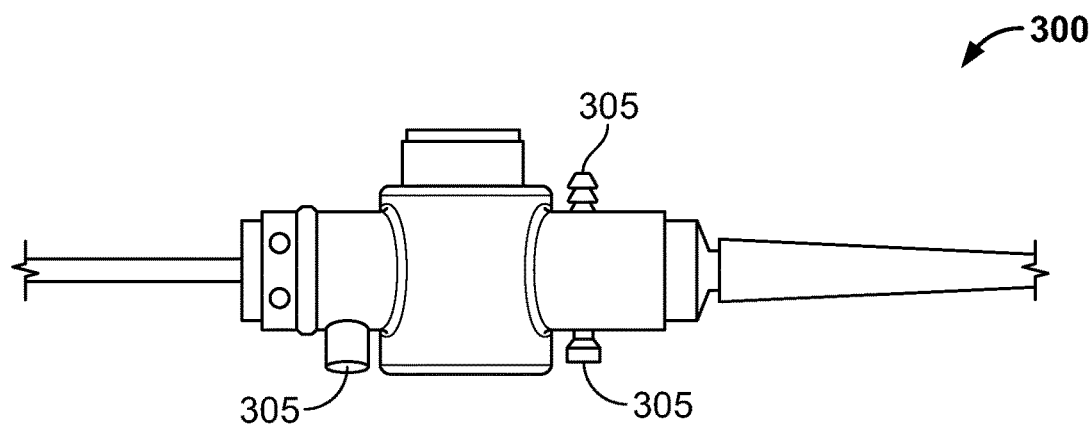
FIG. 3 is a close-up illustration of a connector of an endoscope depicting a plurality of ports.

FIG. 2 is a close-up illustration of a plurality of ports on an endoscope 202. FIG. 2 illustrates an auxiliary water port 205, a water jet connector inlet port 210, and additional ports 208, 209. In an embodiment, each port may be closed off by means of a compression fitting 215 described in subsequent sections of the present specification. FIG. 3 illustrates a connector 300 of an endoscope showing a plurality of ports 305.

Figure 4A:
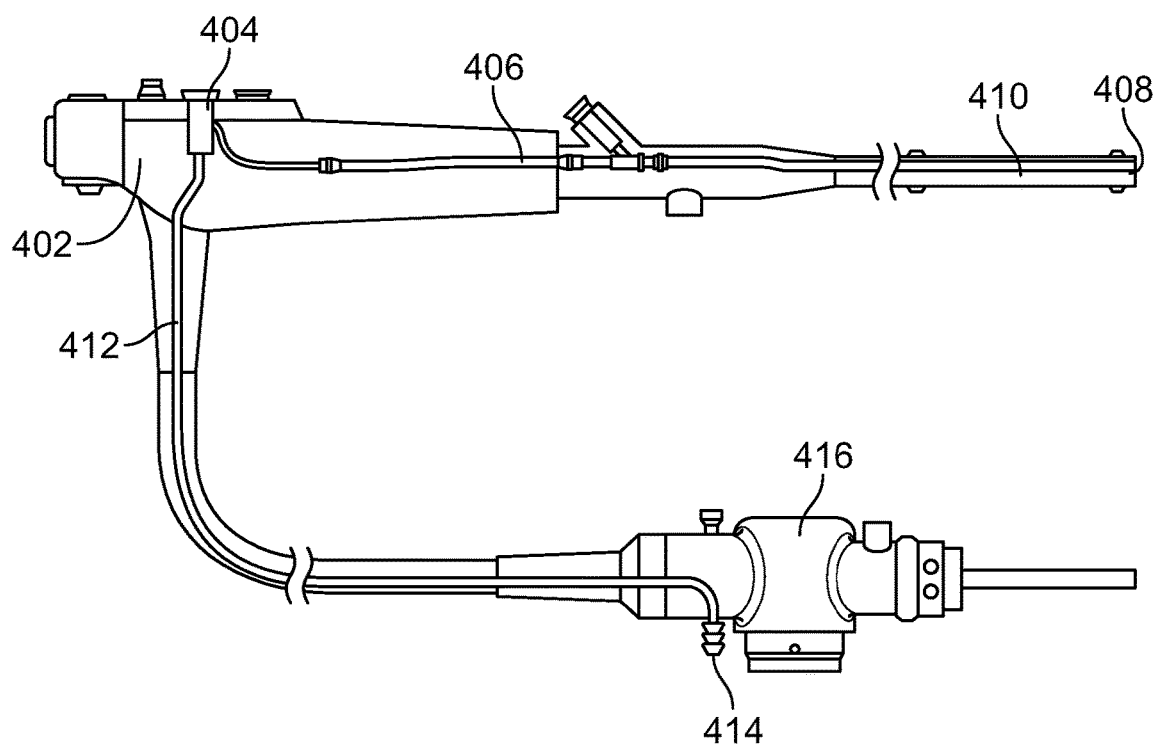
FIG. 4A is a cross-sectional illustration of an endoscope, depicting a suction channel extending through the endoscope body.

FIG. 4A is a cross-sectional illustration of an endoscope 400, depicting a suction channel extending through the endoscope body. A handle 402 of endoscope 400 comprises a suction cylinder 404 which is connected with a first portion of a suction channel 406 extending to a distal tip 408 of an insertion tube 410, and is used to provide suction when insertion tube 410 is inserted within a patient's body. The suction channel 406 may also be used as a biopsy channel. The suction cylinder 404 is also connected with a second portion of a suction channel 412 which extends to a suction port 414 of a connector 416. During reprocessing, it is essential to sterilize the entire suction channel thoroughly.

Figure 4B:
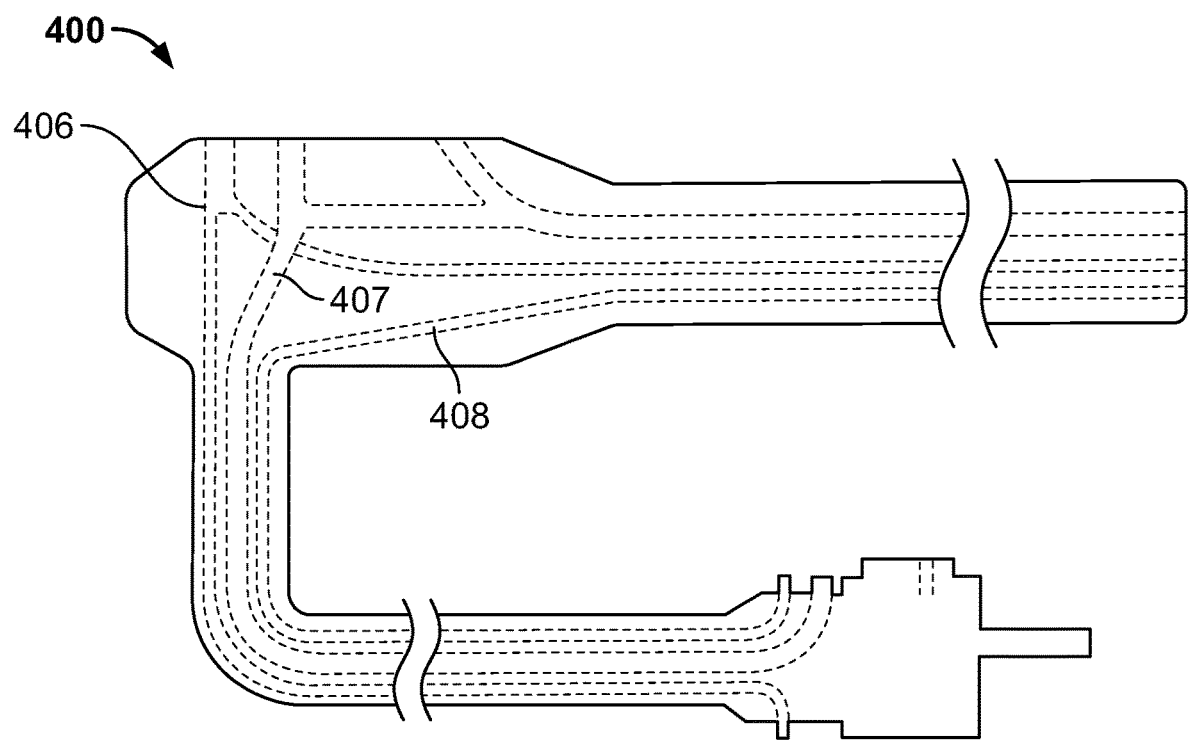
FIG. 4B is a cross-sectional illustration of an endoscope, depicting a plurality of channels extending through the endoscope body.

FIG. 4B is a cross-sectional illustration of an endoscope 400, depicting a plurality of channels 406, 407, 408, extending through the endoscope body.

Figure 5A:
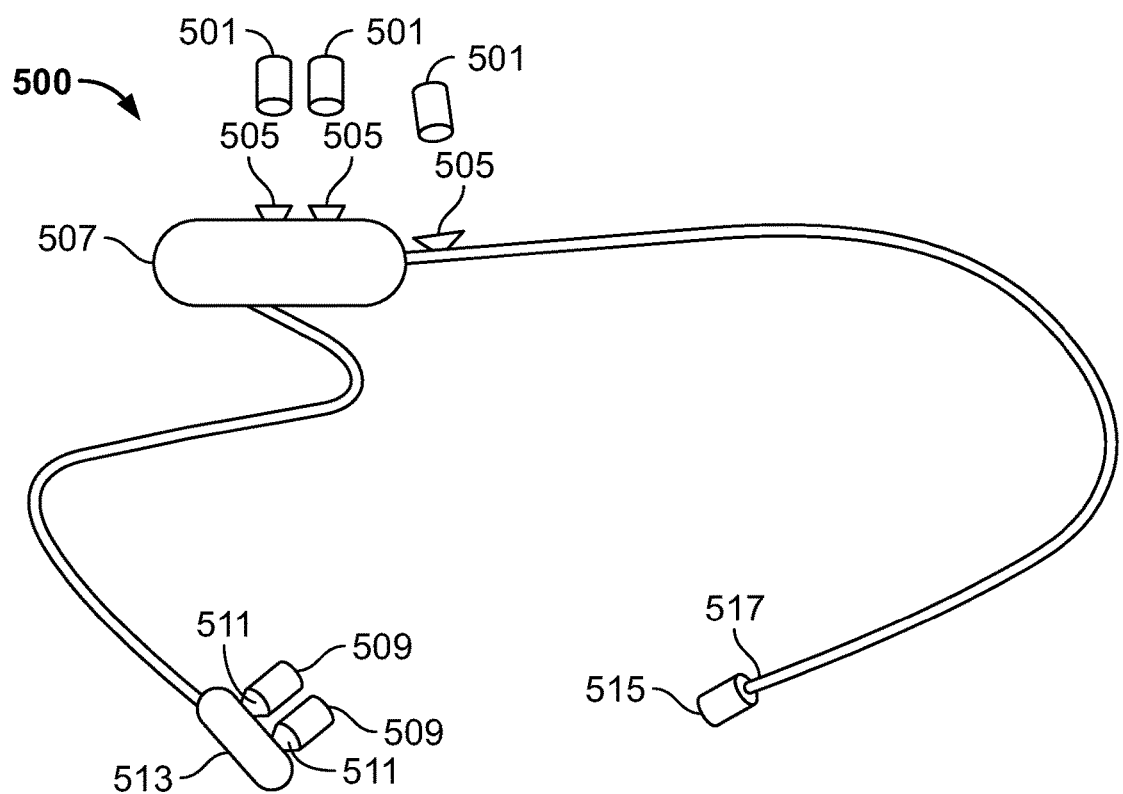
FIG. 5A is an illustration of an endoscope depicting an embodiment of pressure resistant fittings for covering a plurality of ports on the endoscope.

FIG. 5A is an illustration of an endoscope 500 and pressure resistant fittings 501, 509, 515 used for covering a plurality of ports on the endoscope 500, in accordance with an embodiment. The pressure resistant fittings 501 are intended to close the ports 505 provided on a handle 507 of the endoscope 500. Similar pressure fittings 509 are used to cover/seal off port openings 511 provided on a connector portion 513 during sterilization and reprocessing of the endoscope 500. In embodiments, a pressure fitting 515 is also provided for sealing off the endoscope's tip 517. The pressure fittings resist the forces of the pressure of sterilization medium within the endoscope channels.

Figure 5B:
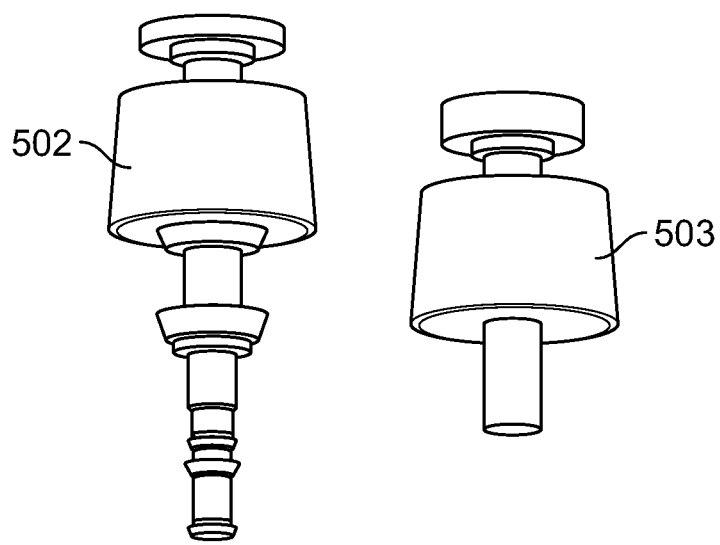
FIG. 5B is an illustration of compression fittings in accordance with one embodiment of the present specification.

FIG. 5B is an illustration of compression fittings 502, 503 in accordance with one embodiment of the present specification. In an embodiment, the compression fittings 502, 503 are pressure resistant connectors which connect openings (such as ports 505, 511 and tip 517 shown in FIG. 5A) on the endoscope to a steam generator and allow the passage of super-heated steam through and into the endoscope channels for sterilization of the channels. In embodiments, any pressure resistant connections known in the field, such as but not limited to luer and spring loaded locking mechanisms, may be used as compression fittings 502, 503. In some embodiments, the compression fittings 502, 503 are able to withstand a pressure of at least 15 psi or 1 PSIG, desirably a pressure of at least 20 psi or 6 PSIG, and most desirably a pressure of at least 30 psi or 15 PSIG.

Figure 6A:
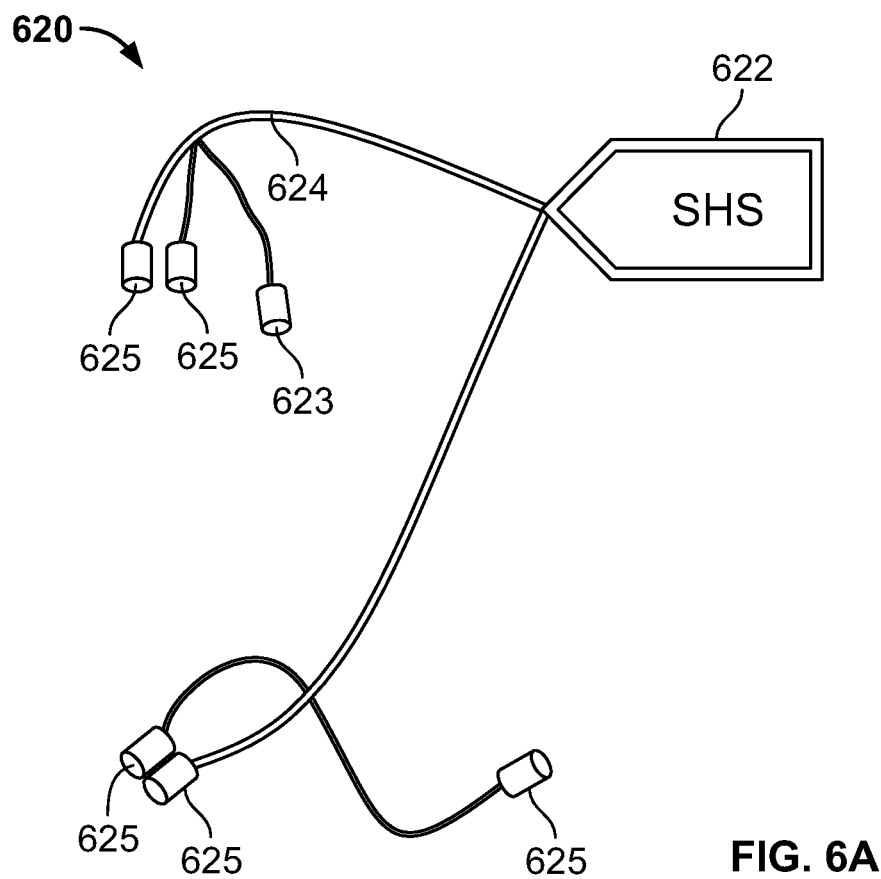
FIG. 6A is an illustration of a system for sterilizing an endoscope using steam, in accordance with one embodiment of the present specification.

FIG. 6A is an illustration of a system 620 for sterilizing an endoscope using steam, in accordance with one embodiment of the present specification. The system 620 comprises a steam generator 622 connected to at least one compression fitting 623 by a length of tubing 624. In embodiments, tubing 624 may be made of a heat resistant material, such as but not limited to Teflon. In various embodiments, steam generator 622 produces super-heated steam at a desired temperature ranging from 120° C. to 135° C. and pressure ranging from 1 Psig to 50 psig. Steam generated by the steam generator 622 travels through the tubing 624 and the compression fitting 623 and into the channels of an endoscope (not shown), pressurizing the channels. Pressure resistant fittings 625 cover the remaining openings to create a closed system and, in some embodiments, are attached to the steam generator so they do not become misplaced. In embodiments, a shape of pressure resistant fittings 625 may be modified according to a corresponding port of the endoscope being fitted with it. Since, fittings 625 are pressure sensitive valves, in embodiments, once a desired pressure is reached within the endoscope's channels, one or more of the fittings 625 open to release excess pressure by allowing the steam to escape, resulting in circulation of the steam at the desired pressure and temperature through the channels.

Figure 6B:
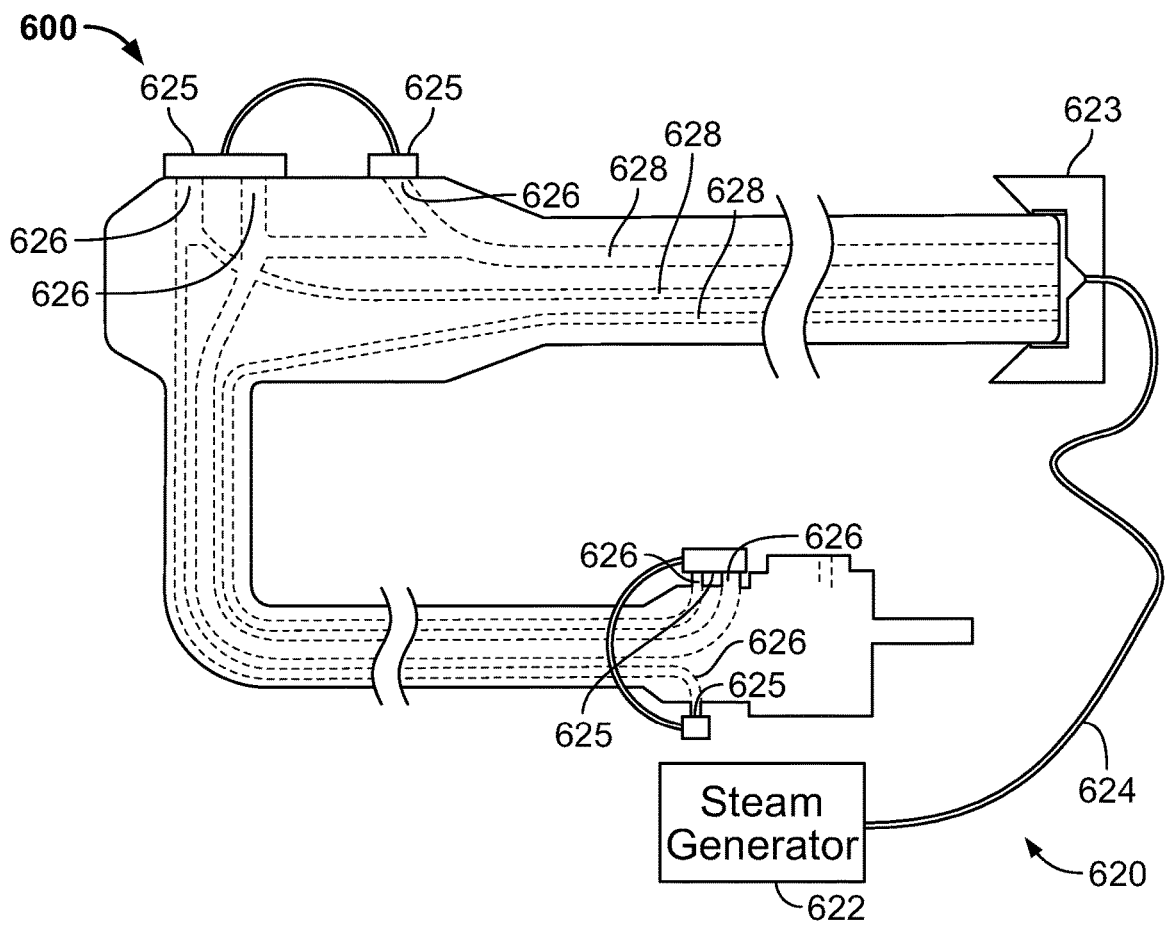
FIG. 6B is another illustration of a system for sterilizing an endoscope using steam, in accordance with another embodiment of the present specification.
Figure 6C:
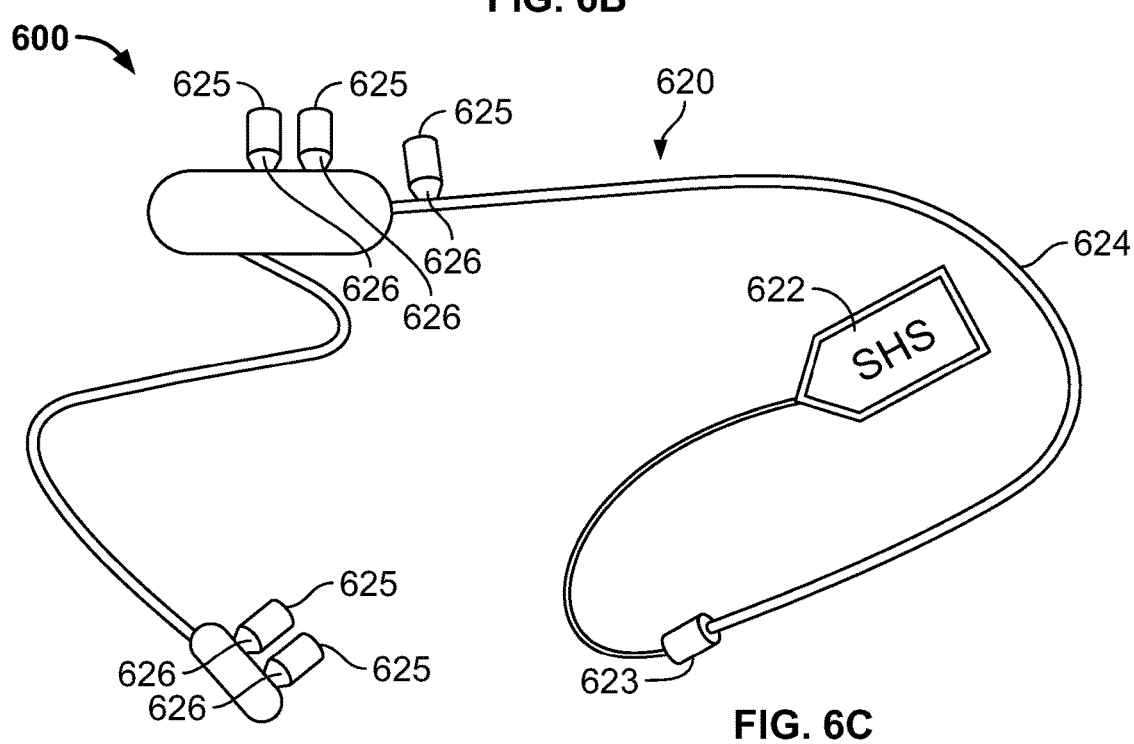
FIG. 6C is an illustration of a system for sterilizing an endoscope using steam, in accordance with another embodiment of the present specification.

FIGS. 6B and 6C are illustrations of a system 620 for sterilizing an endoscope 600 using steam, in accordance with an embodiment of the present specification. FIG. 6B illustrates the sterilization system 620 comprising a steam generator 622 connected to at least one compression fitting 623 by a length of tubing 624. In the embodiment shown in FIGS. 6B and 6C, the steam generator 622 is connected to the pressure fitting 623 applied upon the opening/port provided in a tip of the endoscope 600. Steam generated by the steam generator 622 travels through the tubing 624 and the compression fitting 623 into the channels 628 of the endoscope 600. Pressure resistant fittings 625 cover the remaining ports/openings 626 to create a closed system.

Figure 6D:
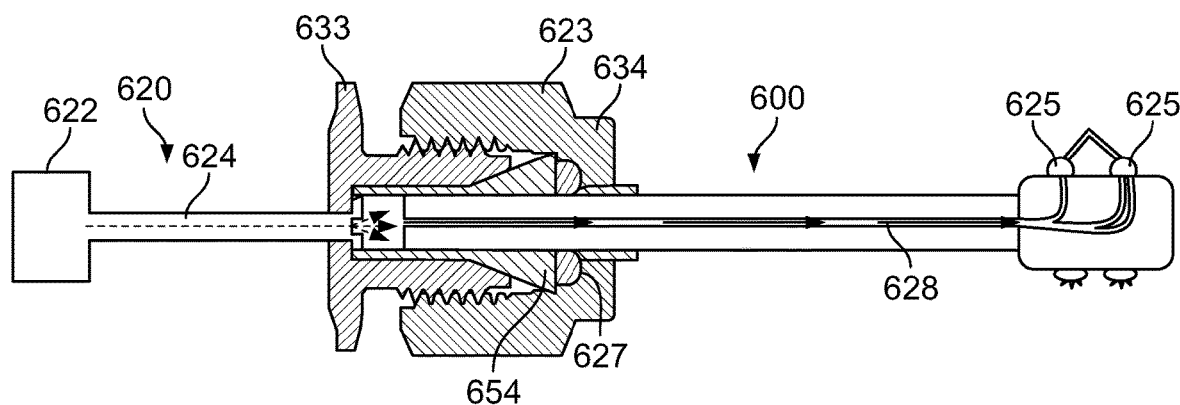
FIG. 6D is an illustration of a system for sterilizing an endoscope using steam, in accordance with another embodiment of the present specification.
Figure 6E:
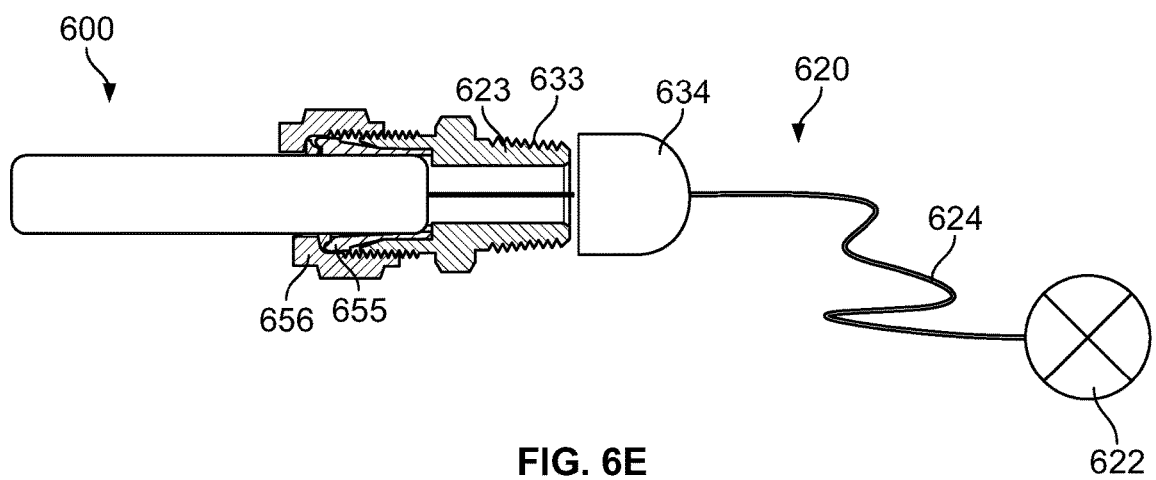
FIG. 6E is an illustration of a system for sterilizing an endoscope using steam, in accordance with another embodiment of the present specification.
Figure 6F:
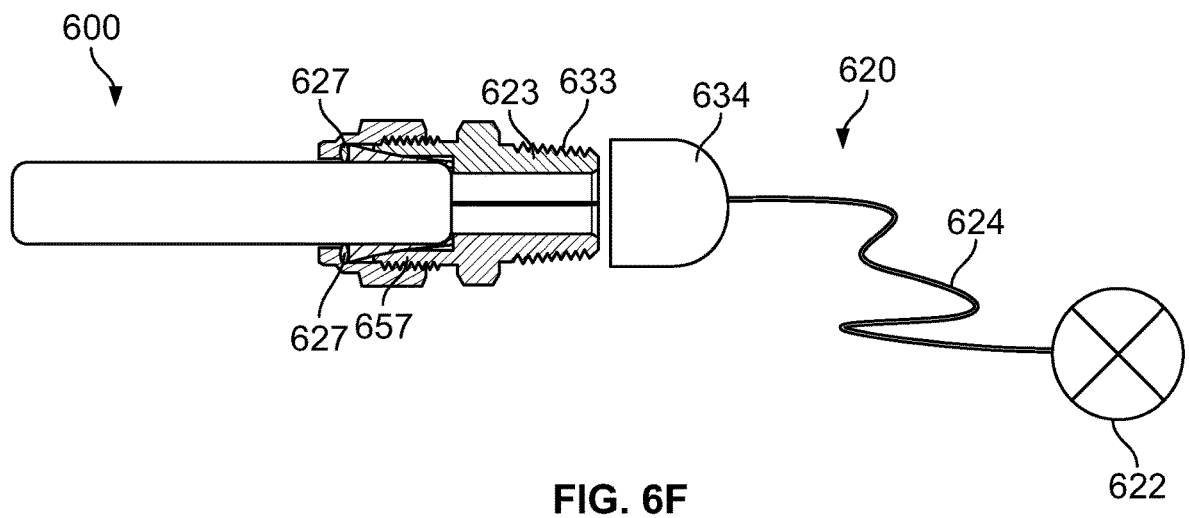
FIG. 6F is an illustration of a system for sterilizing an endoscope using steam, in accordance with another embodiment of the present specification.

FIGS. 6D, 6E and 6F illustrate close up views of the compression fitting shown in FIGS. 6B and 6C. Steam generator 622 delivers steam through delivery tubing 624 and compression fitting 623 into the channels 628 of the endoscope 600. The compression fitting 623 comprises a fitting body 633 onto which a nut 634 is screwed into place to secure the compression fitting 623 to a port of the endoscope 600. Fitting body 633 also comprises a compression ring 654 which get compressed as the nut 634 is tightened creating a seal. In an embodiment, the fitting body 633 is shaped like a cap to fit on the port. The compression fitting 623 is shaped such that it has a flat portion and a ramp portion 654. Referring to FIG. 6E, the compression fitting 623 comprises a flat O-ring connected to a ramp 655 which is in turn connected to an O-ring 656 to provide a better seal. Referring to FIG. 6F, the compression fitting 623 comprises a ramp 657 connected to O ring 627.

Figure 6G:
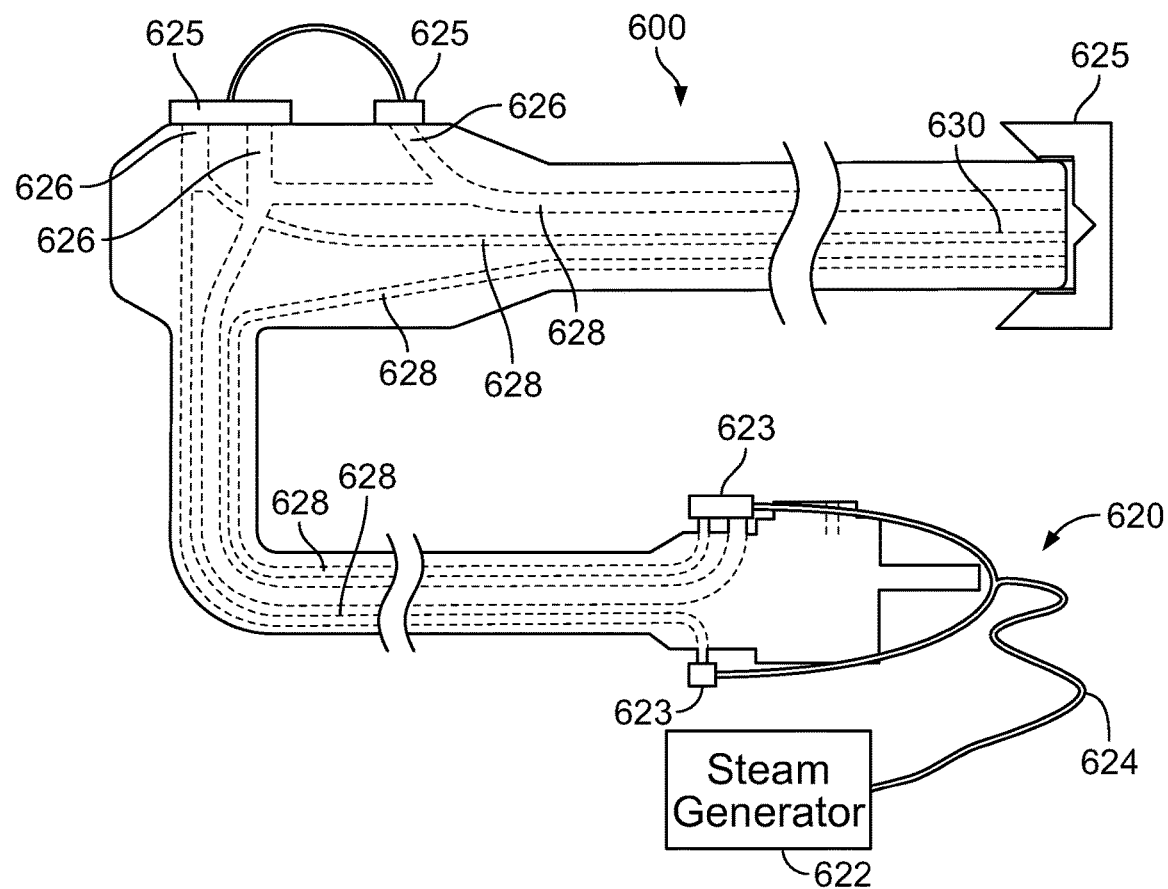
FIG. 6G is an illustration of a system for sterilizing an endoscope using steam, in accordance with another embodiment of the present specification.
Figure 6H:
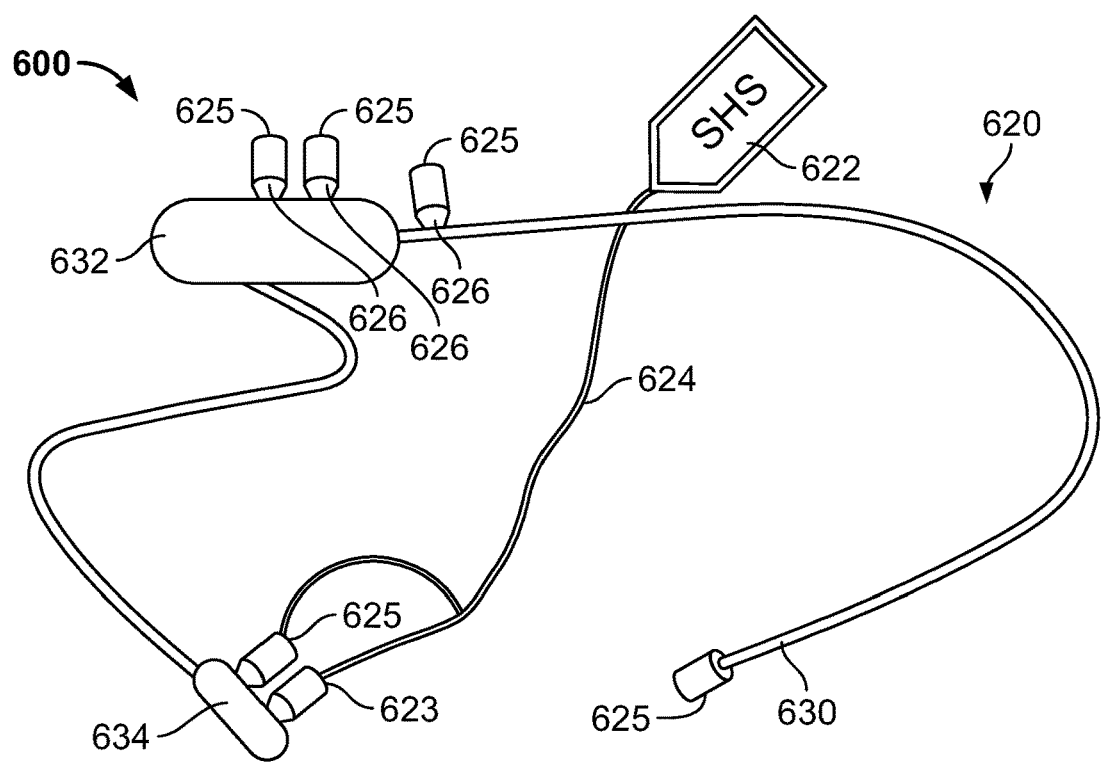
FIG. 6H is an illustration of a system for sterilizing an endoscope using steam, in accordance with another embodiment of the present specification.

FIGS. 6G and 6H are illustrations of a system 620 for sterilizing an endoscope 600 using steam, in accordance with another embodiment of the present specification. FIGS. 6G and 6H illustrate the sterilization system 620 comprising a steam generator 622 connected to at least one compression fitting 623 by a length of tubing 624. In the embodiment shown in FIG. 6G the steam generator 622 is simultaneously connected to two pressure fittings 623 applied upon the two openings/ports provided on a connector of the endoscope 600. In the embodiment shown in FIG. 6H the steam generator 622 is connected to a pressure fitting 623 applied upon one of the openings/ports provided on a connector 634 of the endoscope 600. Steam generated by the steam generator 622 travels through the tubing 624 and the compression fitting 623 into the channels 628 of the endoscope 600. Pressure resistant fittings 625 cover the remaining ports/openings such as ports 626 in a handle 632 of the endoscope and the opening/port 630 in the tip of the endoscope to create a closed system.

Figure 6I:
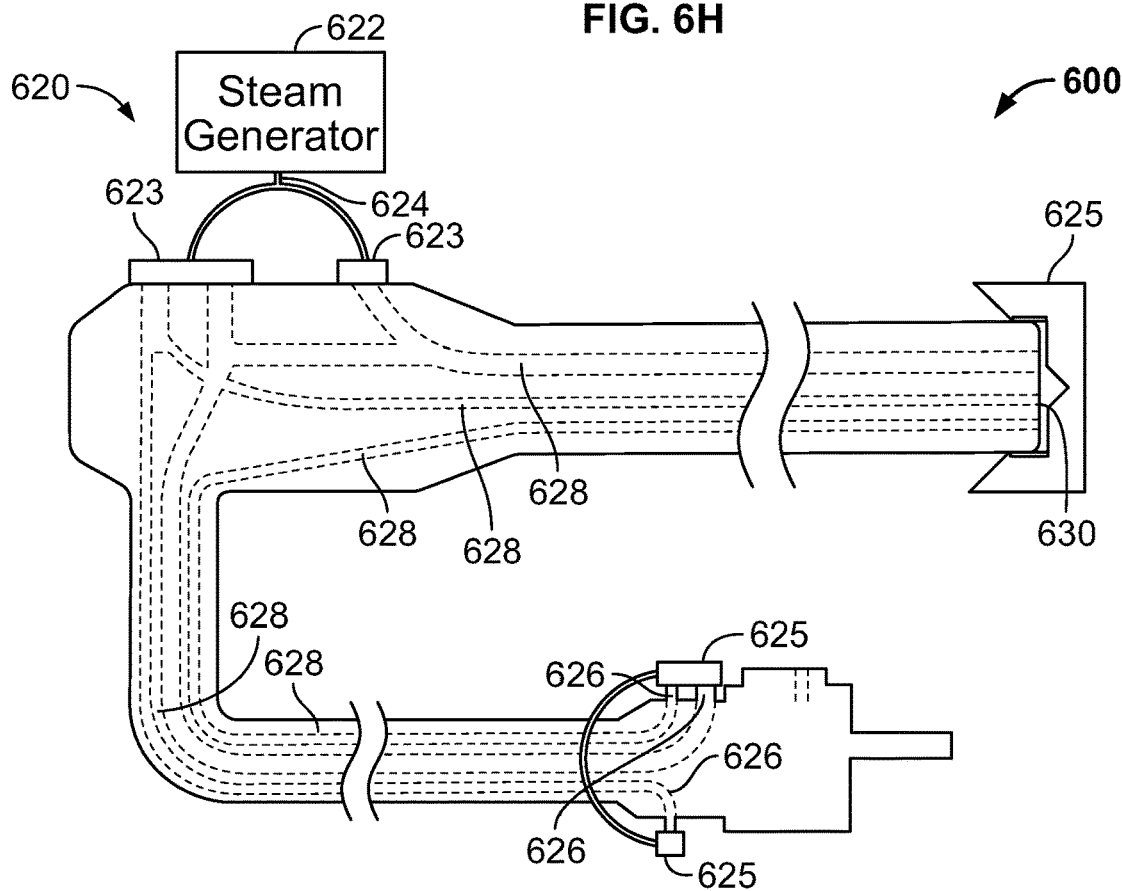
FIG. 6I is an illustration of a system for sterilizing an endoscope using steam, in accordance with another embodiment of the present specification.
Figure 6J:
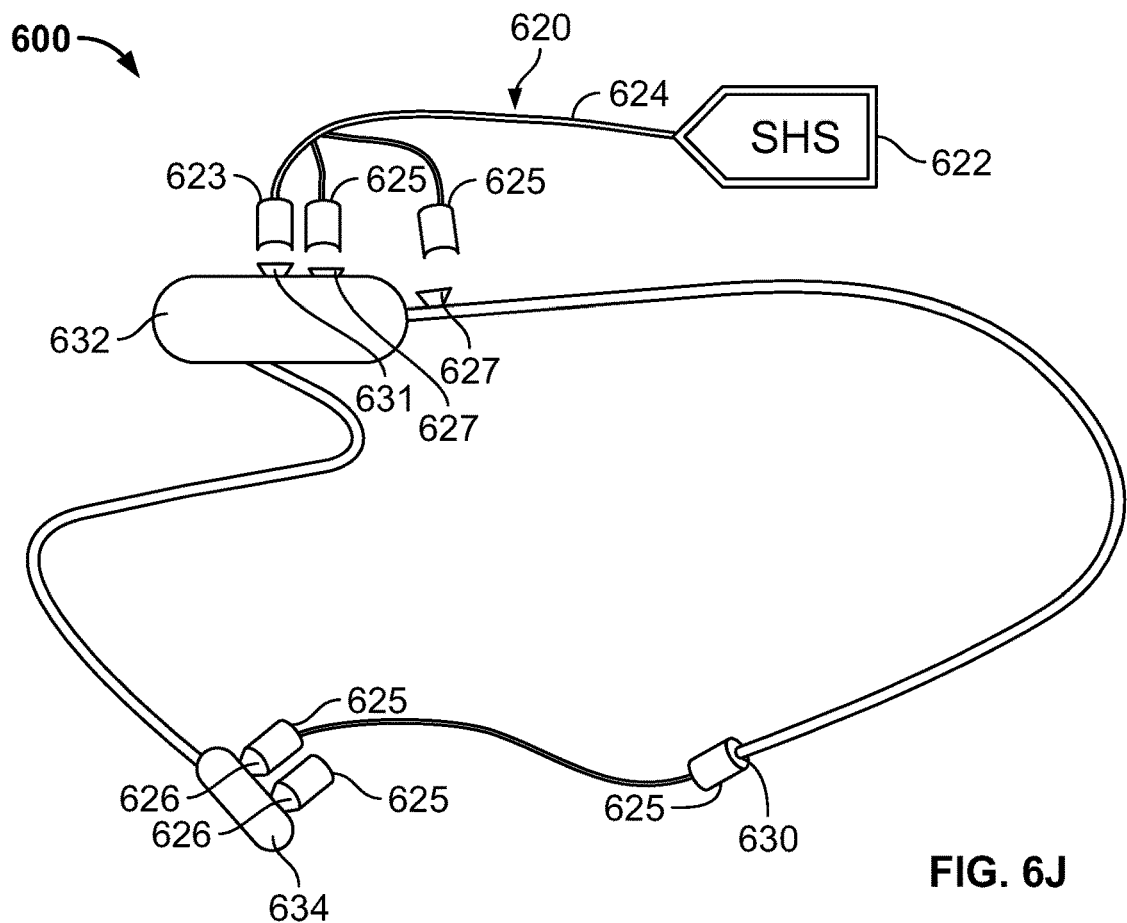
FIG. 6J is an illustration of a system for sterilizing an endoscope using steam, in accordance with yet another embodiment of the present specification.

FIGS. 6I and 6J are illustrations of a system 620 for sterilizing an endoscope 600 using steam, in accordance with another embodiment of the present specification. FIGS. 6I and 6J illustrate the sterilization system 620 comprising a steam generator 622 connected to at least one compression fitting 623 by a length of tubing 624. In the embodiment shown in FIG. 6I the steam generator 622 is simultaneously connected to pressure fittings 623 applied upon all the openings/ports provided on a handle of the endoscope 600. In the embodiment shown in FIG. 6J, the steam generator 622 is connected to a pressure fitting 623 applied upon one of the openings/ports 631 provided on a handle 632 of the endoscope 600. Steam generated by the steam generator 622 travels through the tubing 624 and the compression fitting(s) 623 into the channels 628 of the endoscope 600. Pressure resistant fittings 625 cover the remaining ports/openings 626, 627 the endoscope and the opening/port 630 in the tip of the endoscope 600 to create a closed system.

Figure 7A:
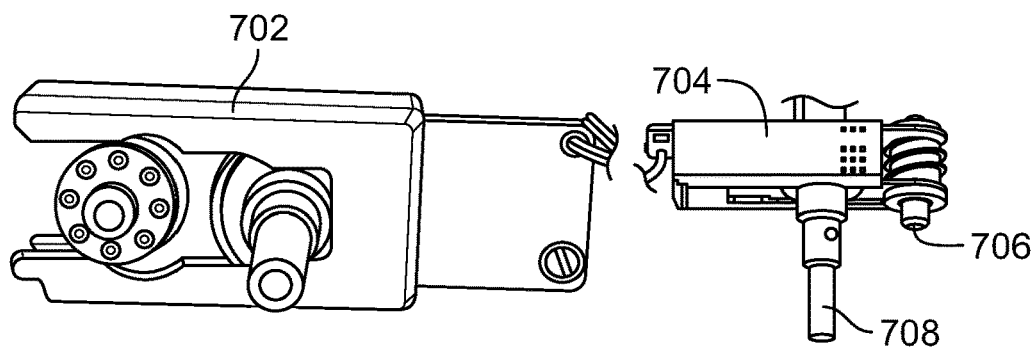
FIG. 7A is an illustration of a compression fitting to connect a steam generator to an endoscope for sterilization, in accordance with one embodiment of the present specification.
Figure 7A:
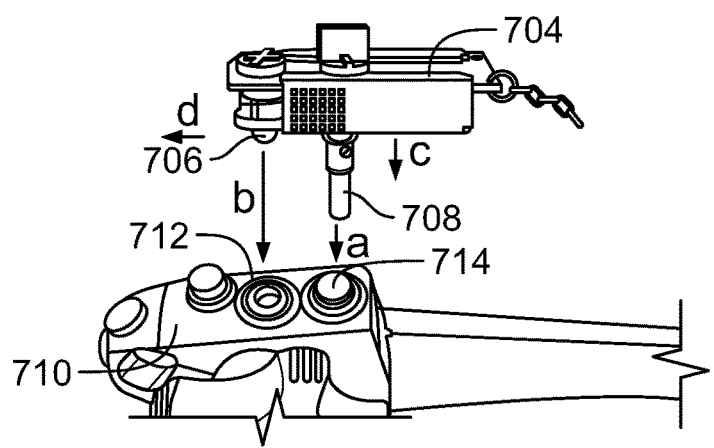

FIG. 7A is an illustration of a compression fitting for connecting with a control section of an endoscope, in accordance with one embodiment of the present specification. Compression fitting/plug 702 comprises a plug frame 704 comprising a protruding suction plug 706 and an air/water plug 708. As shown, the suction plug 706 is used to plug the suction opening 712 provided on a control section 710 or handle of an endoscope and the air/water plug 708 is used to plug the air/water opening 714. In various embodiments, the suction plug 706 is inserted into the suction opening 712 and the air/water plug 708 is inserted into the air/water opening 714 on the control section 710 in order to seal off the endoscope from the outside, thereby providing a pressurized atmosphere within when a steam generator is used to fill the internal channels of the endoscope with steam. In an embodiment, a steam generator may be coupled with the compression fitting 702.

Figure 7B:
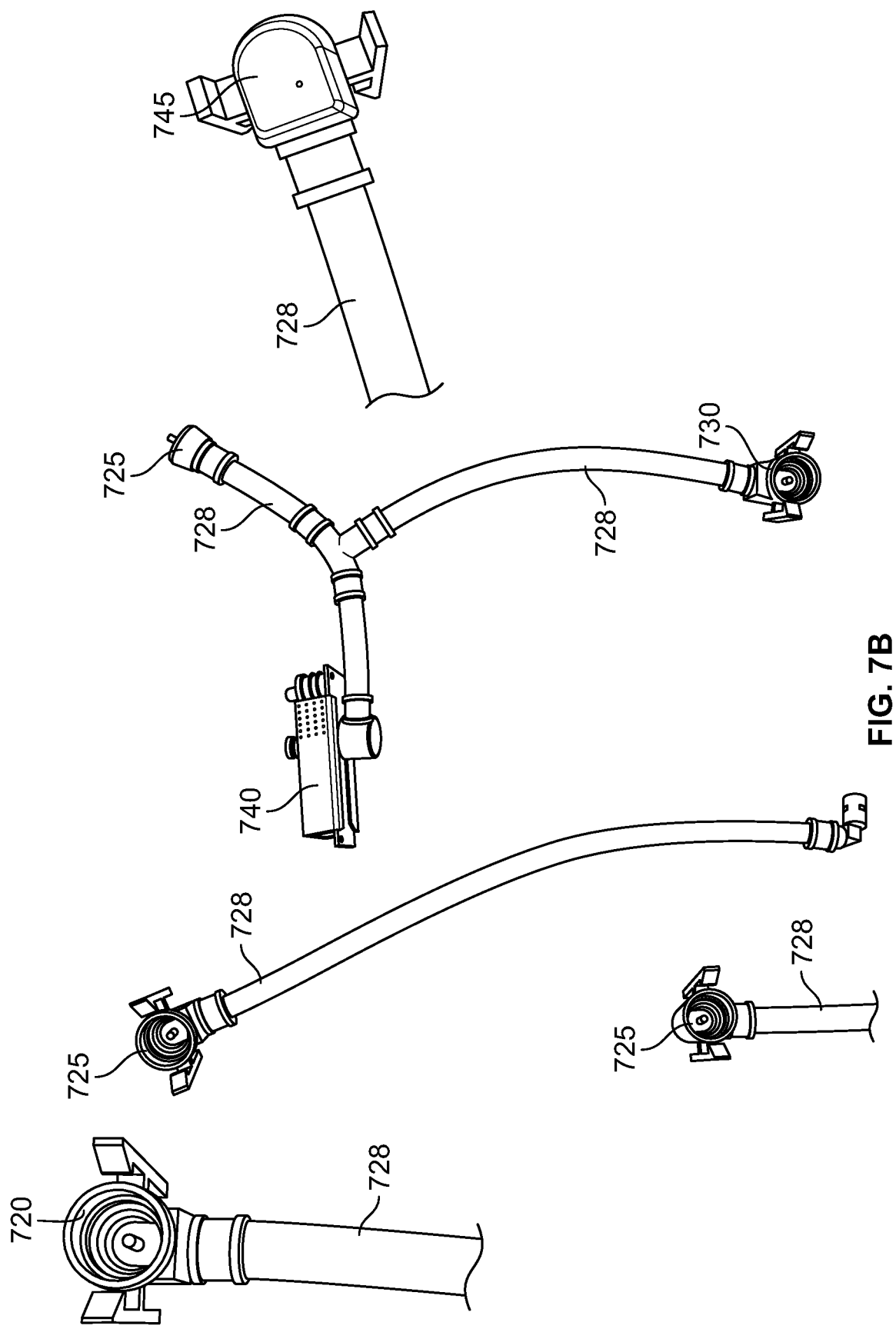
FIG. 7B is an illustration of a plurality of compression fittings to connect a steam generator to an endoscope for sterilization, in accordance with various embodiments of the present specification.

FIG. 7B is an illustration of a plurality of compression fittings to connect a steam generator to an endoscope for sterilization, in accordance with various embodiments of the present specification. Each compression fitting 720, 725, 730, 735, 740 and 745 is connected to a length of tubing 728 which in turn is connected to a steam generator. In embodiments, the shape of each compression fitting 720, 725, 730, 735, 740 and 745 is adapted according to a corresponding port of the endoscope being fitted with it Compression fitting 740 is designed for fitting over a control section of an endoscope such as described with reference to FIG. 7A.

Figure 7C:
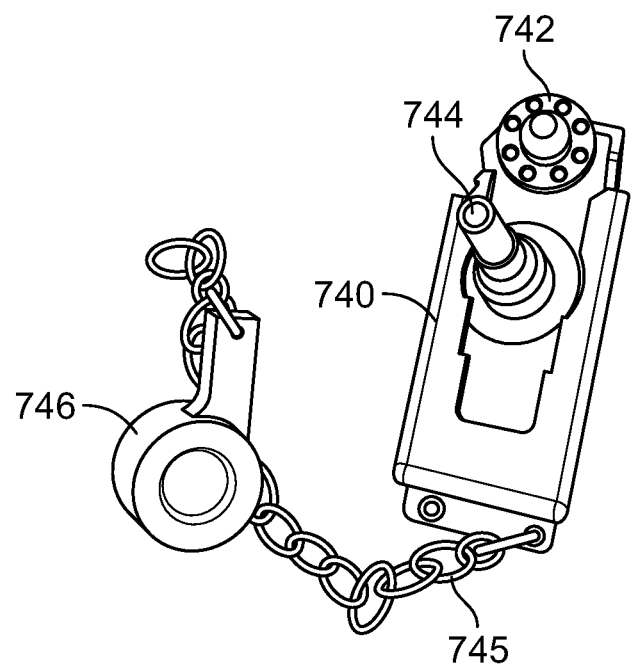
FIG. 7C is an illustration of a plurality of compression fittings used to connect a steam generator to an endoscope for sterilization, in accordance with other embodiments of the present specification.

FIG. 7C is an illustration of a compression fitting for connecting with a control section of an endoscope, in accordance with one embodiment of the present specification. Compression fitting/plug 740 comprises a plug frame comprising a protruding suction plug 742 and an air/water plug 744. In some embodiments, the compression fitting 740 includes a pressure resistant cover 746 for sealing off an opening of one of the channels. The cover 746 is attached to the plug 740 via a length of chain 745. The component 740 slides over the opening on the channels of the endoscope, locking the fitting 740 and 742 into the adjacent channel openings of the endoscope.

Figure 7D:
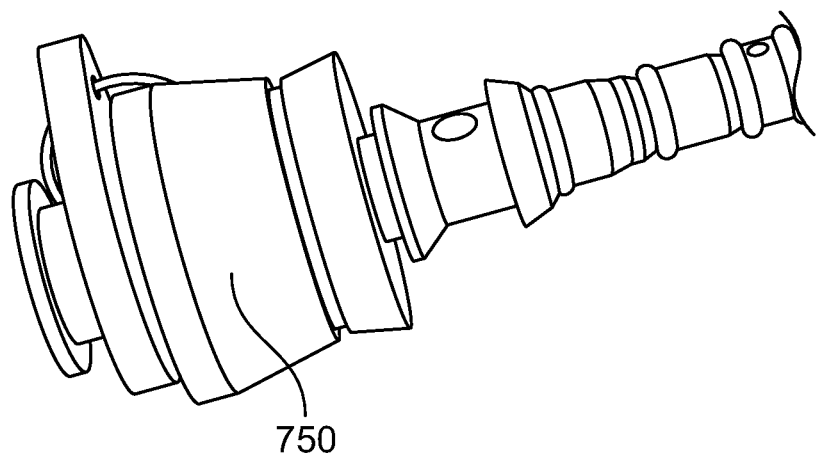
FIG. 7D is an illustration of a compression fitting connected to an endoscope for sterilization, in accordance with various embodiments of the present specification.

FIG. 7D is an illustration of another compression fitting 750, in accordance with one embodiment of the present specification.

Figure 7E:
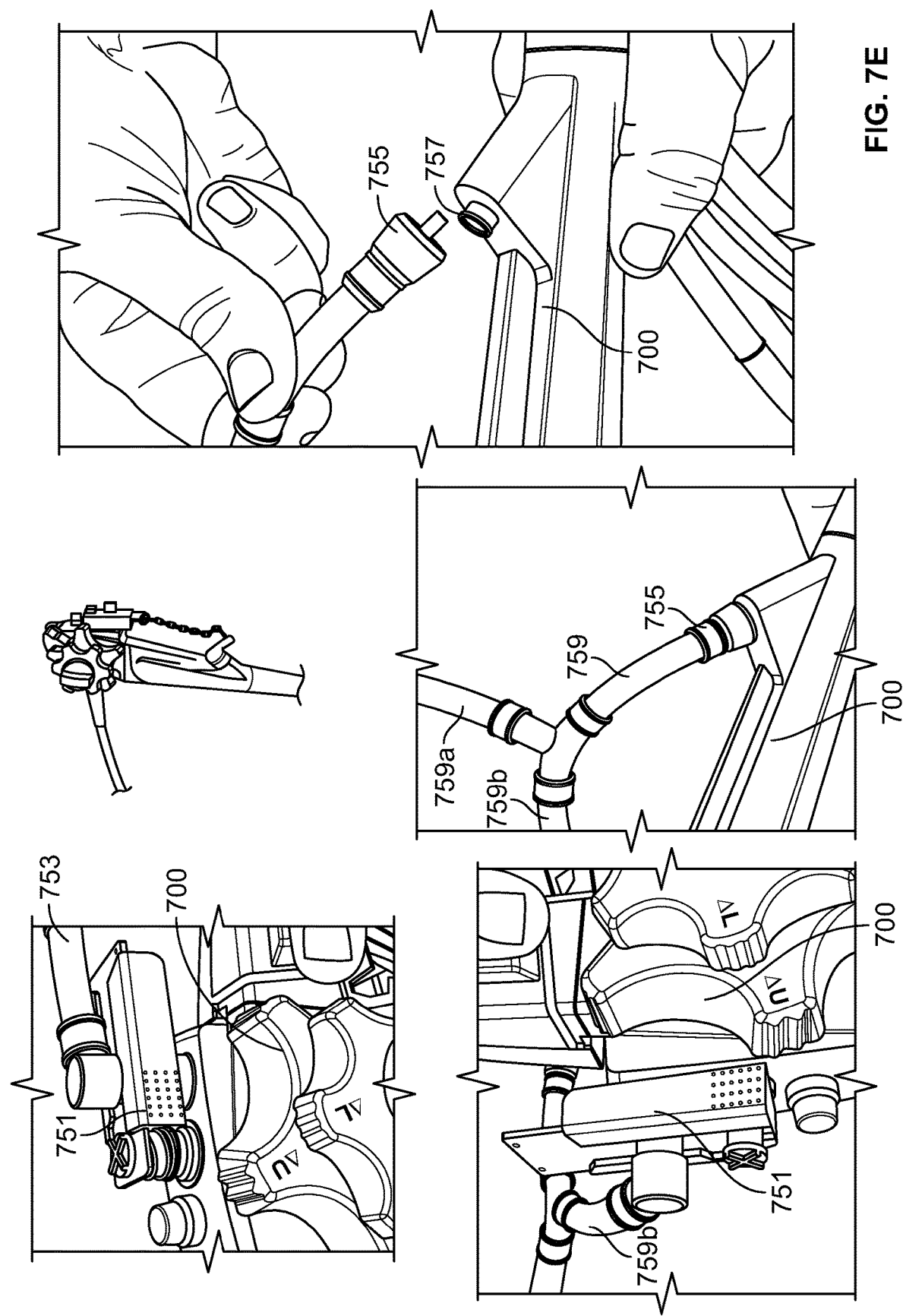
FIG. 7E is an illustration of a plurality of compression fittings connecting a steam generator to an endoscope for sterilization, in accordance with various embodiments of the present specification.

FIG. 7E is an illustration of a plurality of compression fittings connected to an endoscope for sterilization of the same, in accordance with various embodiments of the present specification. A compression fitting 751 is shown fitted on the suction and air/water ports of a handle of the endoscope 700. Compression fitting 751 is connected to a steam generator (not shown in FIG. 7E) via tubing 753. Another compression fitting 755 is connected to a biopsy port 757 of endoscope 700. The compression fitting 755 may be connected to a steam generator via tubing 759 which may bifurcate into two tubing branches 759a and 759b, wherein one of the tubing branches may be connected to a compression fitting applied on another port of the endoscope and the other tubing branch may be connected to a steam source.

Figure 7G:
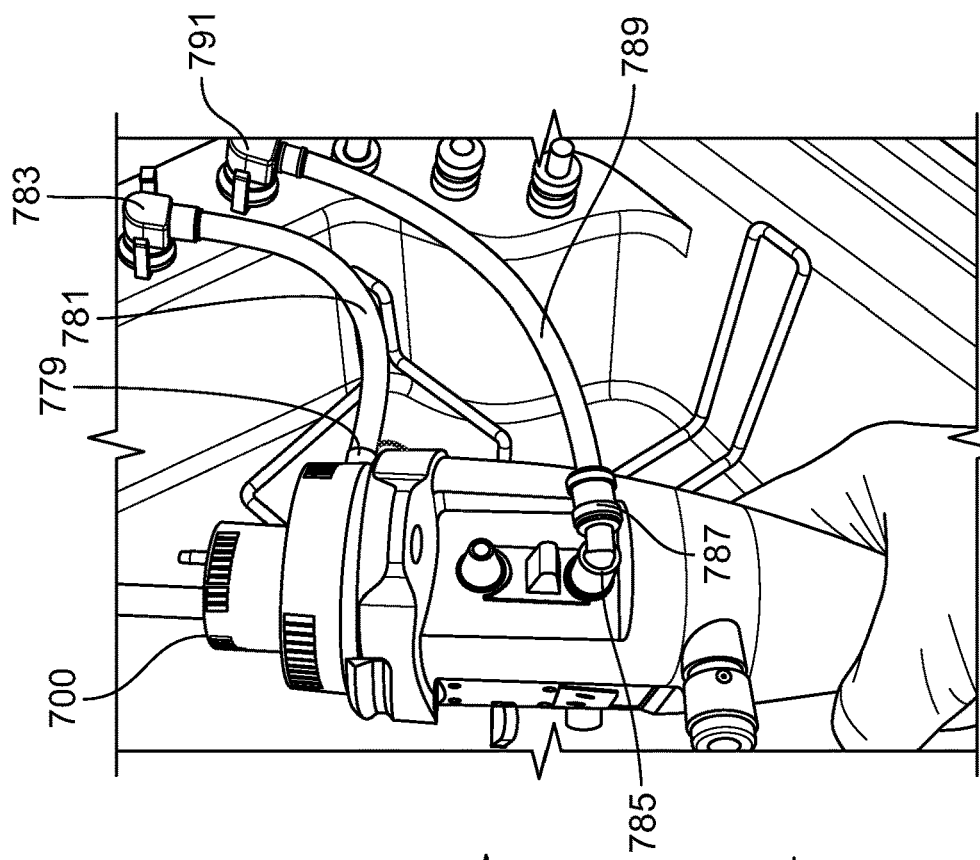
FIG. 7G is an illustration of a compression fitting connected to an endoscope for sterilization, in accordance with another embodiment of the present specification.
Figure 7F:
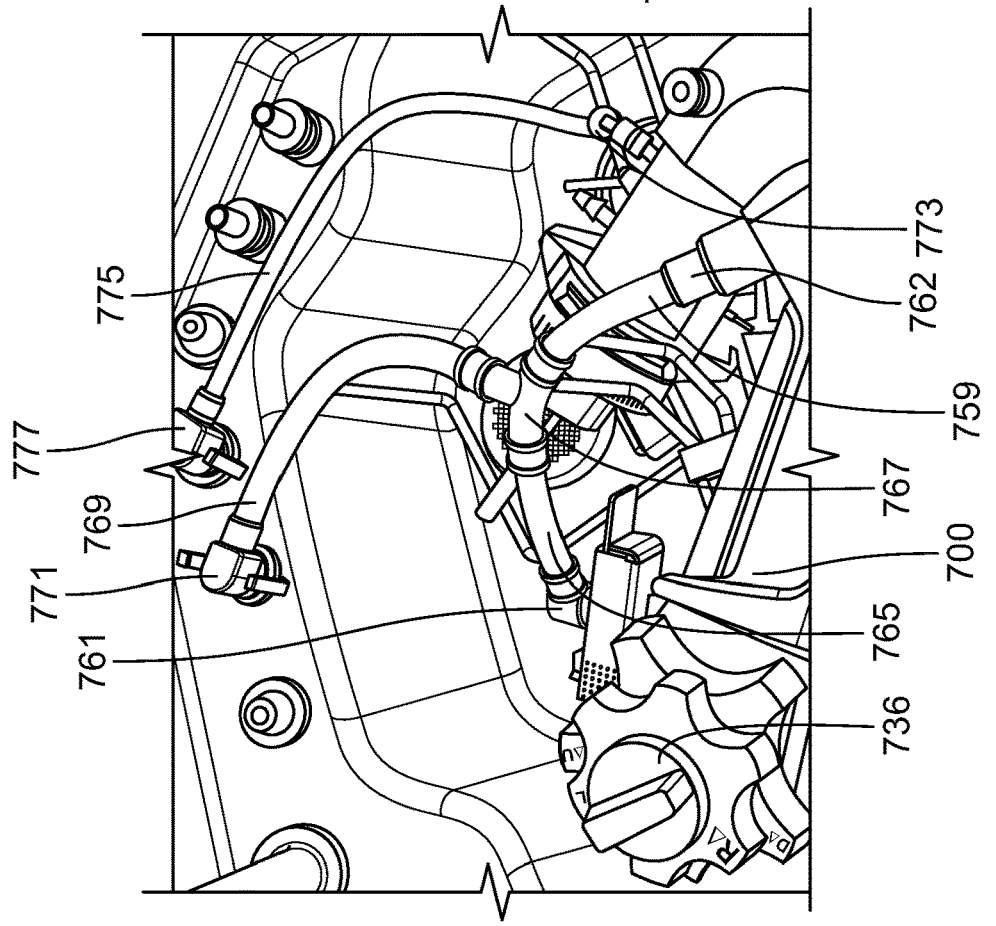
FIG. 7F is an illustration of compression fittings connected to an endoscope for sterilization, in accordance with an embodiment of the present specification.

FIG. 7F is an illustration of a plurality of compression fittings connecting a steam generator to an endoscope 700 for sterilization, in accordance with various embodiments of the present specification. A compression fitting 751 is shown fitted on the suction and air/water ports of a handle 763 of the endoscope 700. Compression fitting 761 is connected to a tubing 765 which is connected to a steam generator (not shown in FIG. 7F) via a three way connector 767, tubing 769 and fitting 771. Another compression fitting 773 is connected to a biopsy port of endoscope 700. The compression fitting 773 is be connected to a steam generator via tubing 775 and fitting 777. FIG. 7G illustrates a connector of an endoscope connected to a steam source for sterilization process, in accordance with an embodiment of the present specification. A first port of the connector 779 is connected to a steam source via a compression fitting connected to a tubing 781 and fitting 783. A second port 785 is connected to a steam source via a compression fitting 787, tubing 789 and fitting 791.

Figure 8A:
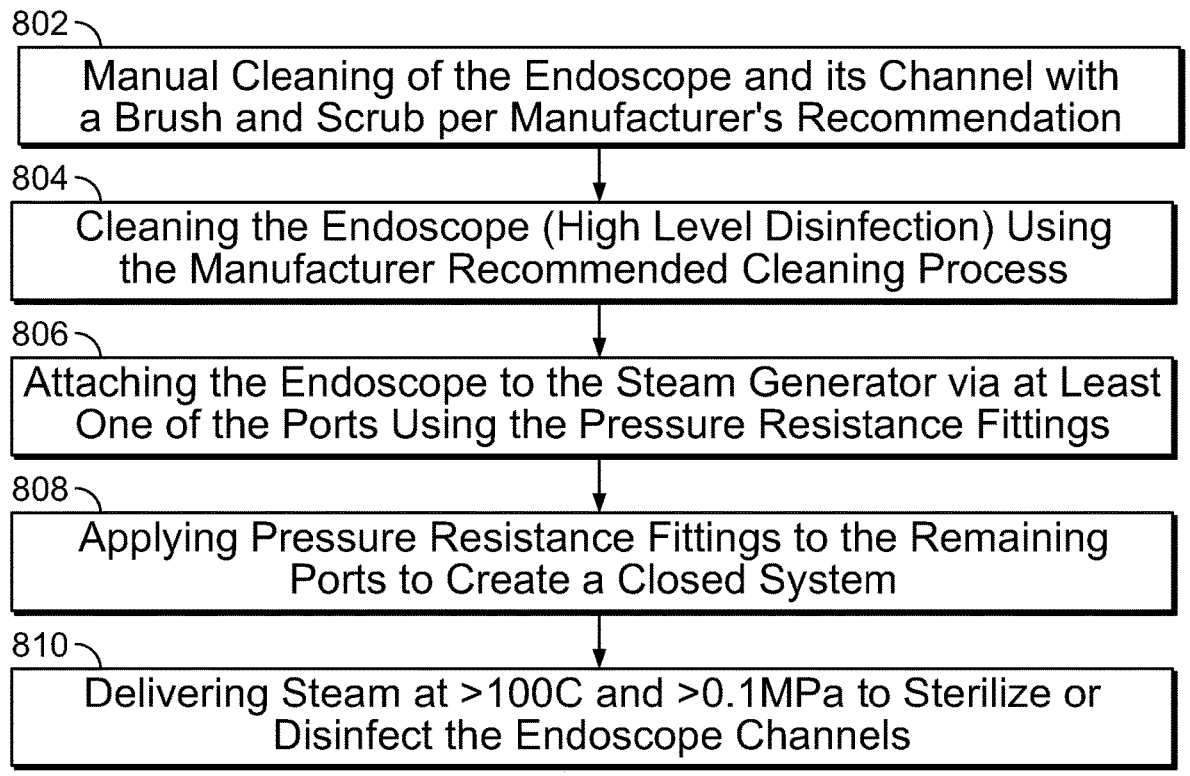
FIG. 8A is a flowchart listing the steps involved in a method of using steam to sterilize an endoscope, in accordance with one embodiment of the present specification.

FIG. 8A is a flowchart listing the steps involved in a method of using steam to sterilize an endoscope, in accordance with one embodiment of the present specification. At step 802, manual cleaning of the endoscope and its channel with a brush and scrub as per the manufacturer's recommendation is performed. Cleaning of the endoscope (High Level Disinfection) using the manufacturer recommended cleaning process is performed at step 804. Then, at step 806, the endoscope is attached to the steam generator via at least one of the ports using pressure resistant compression fittings. Pressure resistant fittings are attached to the remaining ports to create a closed system at step 808. At step 810, steam is delivered at a temperature greater than 100° C. and a pressure greater than 0.1 MPa to sterilize or disinfect the endoscope channels.

Figure 8B:
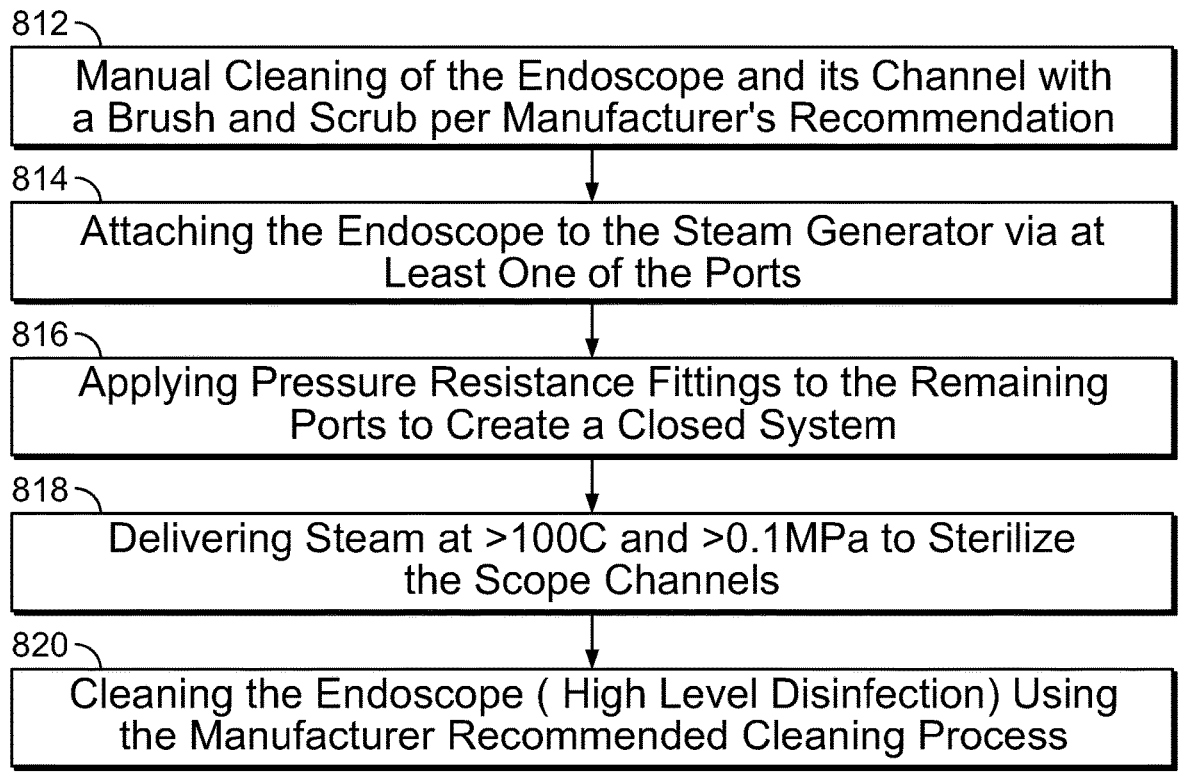
FIG. 8B is a flowchart listing the steps involved in a method of using steam to sterilize an endoscope, in accordance with another embodiment of the present specification.

FIG. 8B is a flowchart listing the steps involved in a method of using steam to sterilize an endoscope, in accordance with another embodiment of the present specification. At step 812, manual cleaning of the endoscope and its channel with a brush and scrub as per the manufacturer's recommendation is performed. Then, at step 814, the endoscope is attached to the steam generator via at least one of the ports using pressure resistant compression fittings. Pressure resistant fittings are attached to the remaining ports to create a closed system at step 816. At step 818, steam is delivered a temperature greater than 100° C. and a pressure greater than 0.1 MPa to sterilize or disinfect the endoscope channels. Cleaning of the endoscope (High Level Disinfection) using the manufacturer recommended cleaning process is then performed at step 820.

Figure 9A:
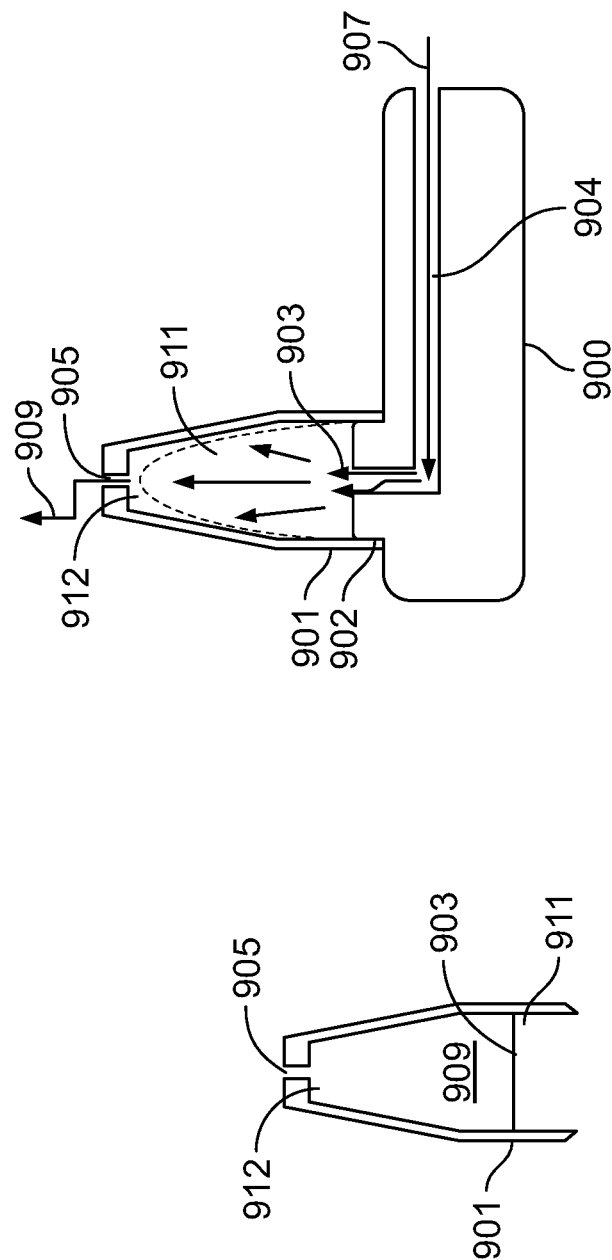
FIG. 9A is an illustration of a pressure resistant fitting including an expandable membrane, in accordance with one embodiment of the present specification.

FIG. 9A is an illustration of a pressure resistant fitting 901 including an expandable membrane 903, in accordance with one embodiment of the present specification. Trapped air 909 in the channel 904 of the endoscope 900 can impair distribution of the steam within the channel, thereby interfering with the sterilization process. Hence, the air 909 in the endoscope channel 904 should escape out of the channel 904 without breaking the seal between the compression fitting 901 and the endoscope port 902 and allow the steam 907 to come in contact with the scope channel 904. To achieve that, an expandable membrane 903 is provided coupled with the compression fitting 901 which divides the chamber in the pressure resistance fitting 901 into two compartments. As the steam 907 enters the channel 904, the air 909 in the channel 904 is pushed into a first compartment 911 out of the scope channel 904, expanding the membrane 903 and out into the second compartment 912 making space for the additional air coming out of the endoscope channel 904 into the first compartment 911. The second compartment 912 has an opening or a one way valve 905 to allow the air 909 in the second compartment 912 to escape, accommodating the expansion of the first compartment 911. The volume of the second compartment 912 is at least 25% of the volume of the air 909 in the scope channel 904, and in an embodiment, the same volume as the air 909 in the scope channel 904 to which it is attached.

Figure 9B:
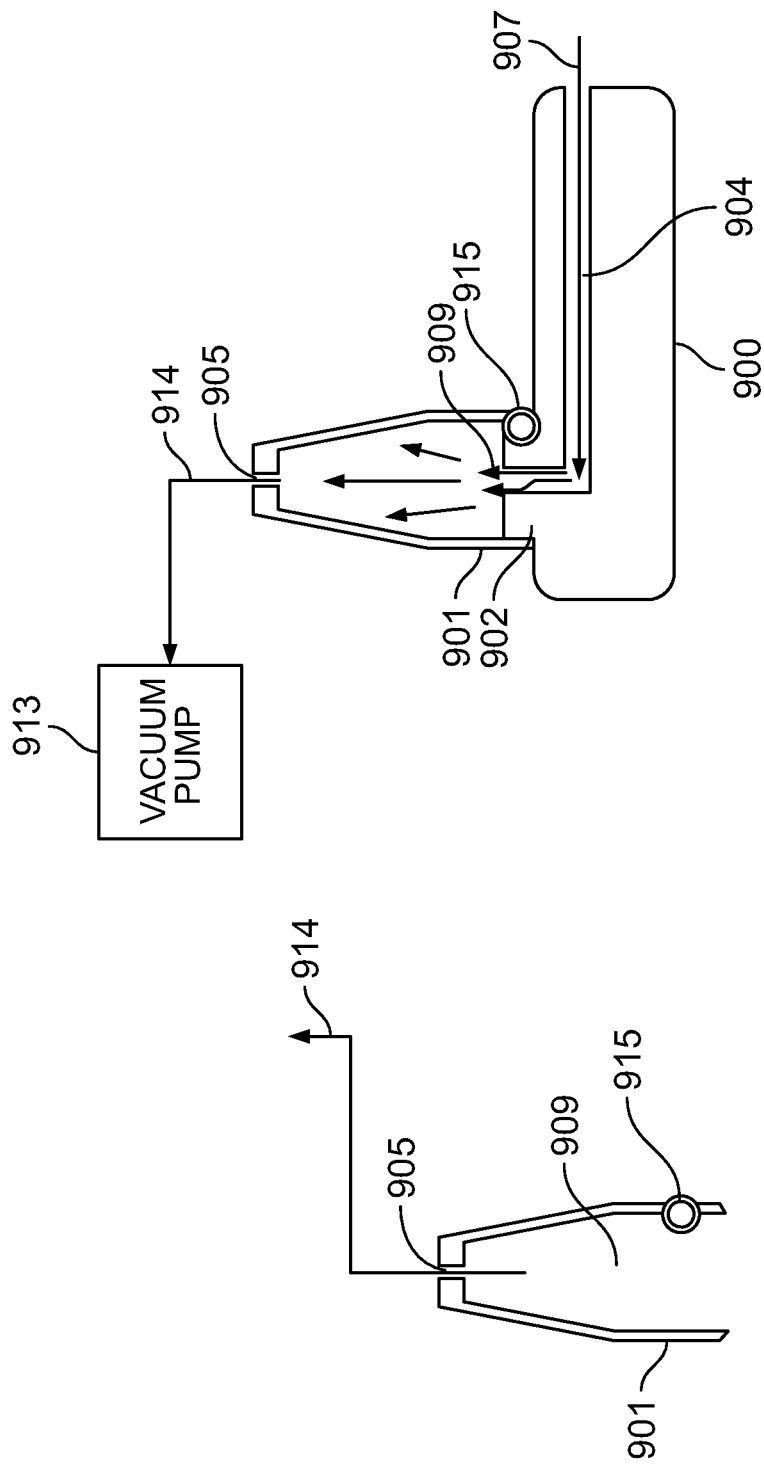
FIG. 9B is an illustration of a pressure resistant fitting including an expandable membrane, in accordance with another embodiment of the present specification.

FIG. 9B is an illustration of a pressure resistant fitting 901 connected to a vacuum pump, in accordance with another embodiment of the present specification. To allow any air 909 trapped in the endoscope channel 904 to escape upon passage of steam 907 in the channel 904 without breaking the seal between the compression fitting 901 and the endoscope port 902, the fitting 901 is connected to a vacuum suction pump 913. As the steam 907 enters the channel 904, the air 909 in the channel 904 is pushed into the fitting 901 and is suctioned away 914 through an opening or one way valve 905. After a specific duration of time, the vacuum pump 913 shuts down while the steam 907 continues to enter the scope channel 904, increasing both its temperature and pressure until the desirable parameters for sterilization or disinfection are reached. After a predetermined time, the suction may be started again, for sucking the steam from the channel 904 and decreasing both the channel 904 pressure and temperature. Alternatively, a temperature sensor 915 is provided coupled to the fitting 901 for sensing the air temperature. As the air temperature approaches a predetermined temperature, the vacuum pump 913 is shut down. After the temperature is maintained at a desirable level for a desirable amount of time, the vacuum pump 913 may be started again for removing the air 909 from the endoscope channel 904.

In various embodiments the various pressure relief valves are controlled by a microprocessor in a sequential fashion so as to ascertain adequate circulation of the sterilizing or disinfecting agent.

Figure 10A:
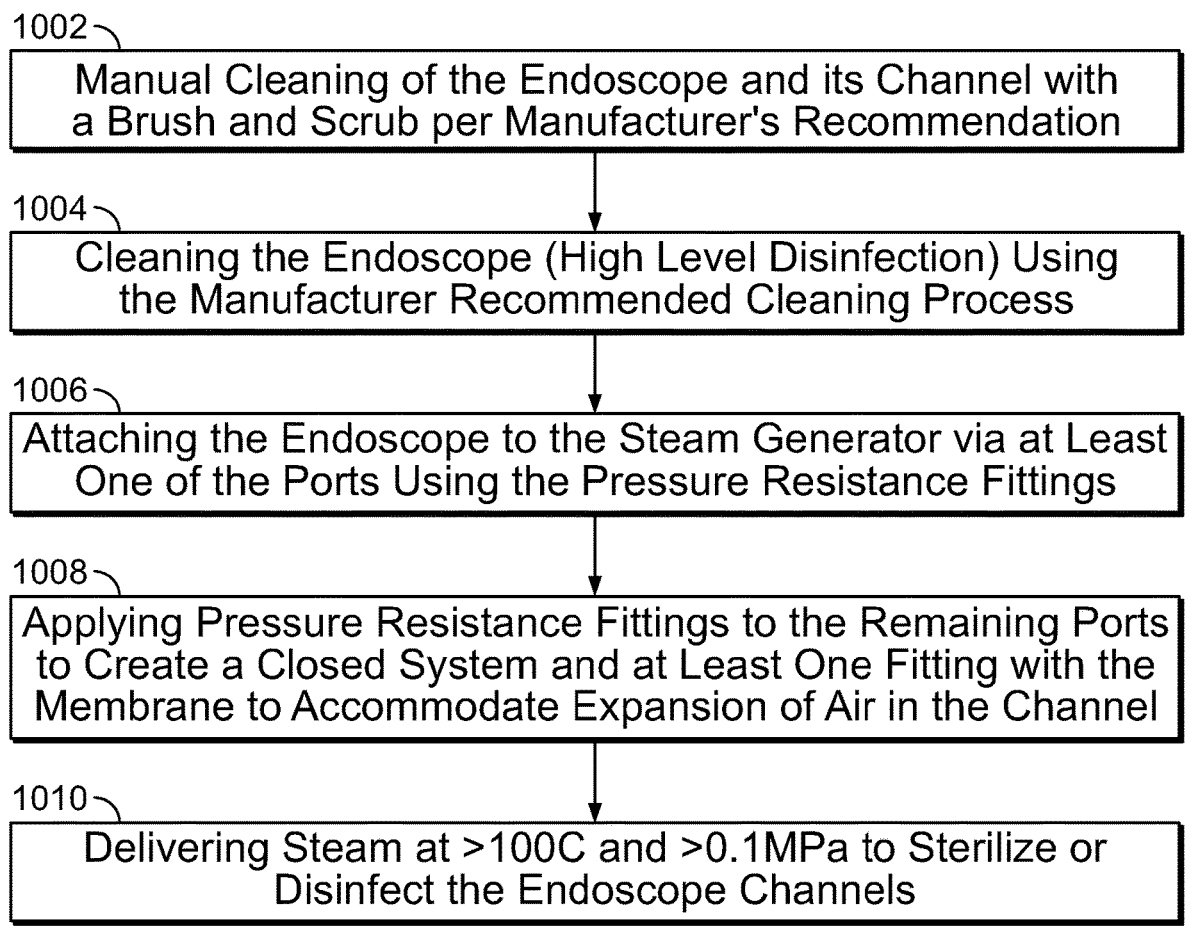
FIG. 10A is a flowchart listing the steps involved in a method of using steam to sterilize an endoscope, in accordance with another embodiment of the present specification.

FIG. 10A is a flowchart listing the steps involved in a method of using steam to sterilize an endoscope, in accordance with another embodiment of the present specification. At step 1002, manual cleaning of the endoscope and its channel with a brush and scrub per the manufacturer's recommendation is performed. Cleaning of the endoscope (High Level Disinfection) using the manufacturer recommended cleaning process is performed at step 1004. Then, at step 1006, the endoscope is attached to the steam generator via at least one of the ports using the pressure resistant compression fittings. Pressure resistant fittings are attached to the remaining ports to create a closed system at step 1008, wherein at least one pressure resistant fitting includes a membrane to accommodate air expansion in an endoscope channel. At step 1010, steam is delivered at a temperature greater than 100° C. and a pressure greater than 0.1 MPa to sterilize or disinfect the endoscope channels.

Figure 10B:
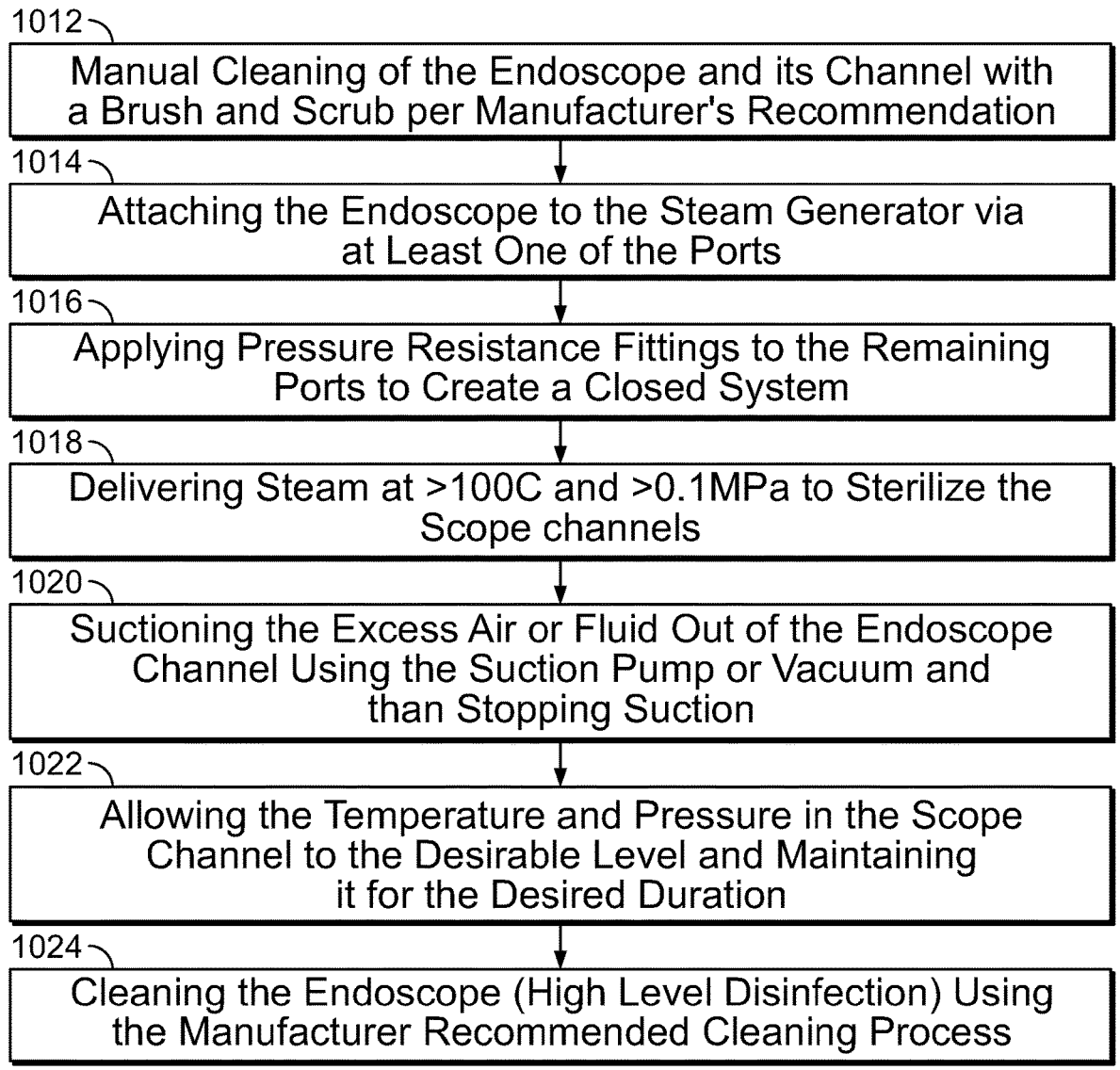
FIG. 10B is a flowchart listing the steps involved in a method of using steam to sterilize an endoscope, in accordance with yet another embodiment of the present specification.

FIG. 10B is a flowchart listing the steps involved in a method of using steam to sterilize an endoscope, in accordance with another embodiment of the present specification. At step 1012, manual cleaning of the endoscope and its channel with a brush and scrub per the manufacturer's recommendation is performed. Then, at step 1014, the endoscope is attached to the steam generator via at least one of the ports using the pressure resistant compression fittings. Pressure resistant fittings are attached to the remaining ports to create a closed system at step 1016. At step 1018, steam is delivered at a temperature greater than 100° C. and a pressure greater than 0.1 MPa to sterilize or disinfect the endoscope channels. Suctioning of excess air or fluid out of the endoscope channel using a suction pump or vacuum, and then the cessation of suction, is performed at step 1020. The temperature and pressure in the endoscope channel are allowed to rise to the desirable level and are maintained at said level for the desired duration at step 1022. Cleaning of the endoscope (High Level Disinfection) using the manufacturer recommended cleaning process is then performed at step 1024.

Figure 11A:
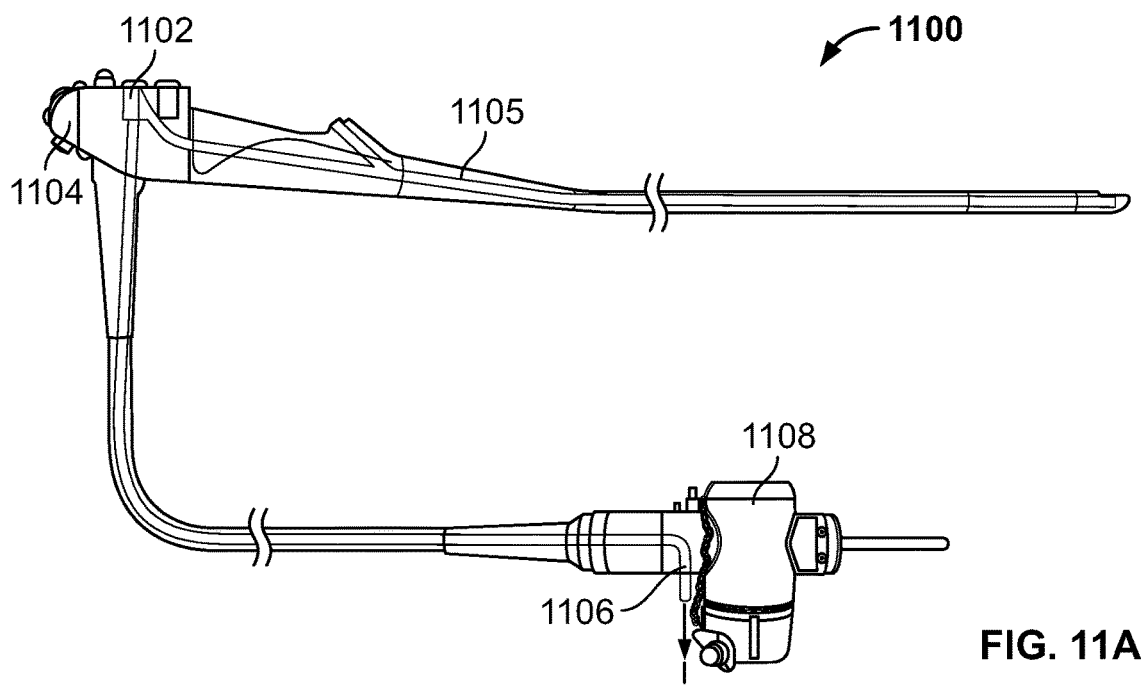
FIG. 11A is a cross-sectional illustration of an endoscope depicting the pathway of steam during a sterilization procedure, in accordance with one embodiment of the present specification.
Figure 11B:
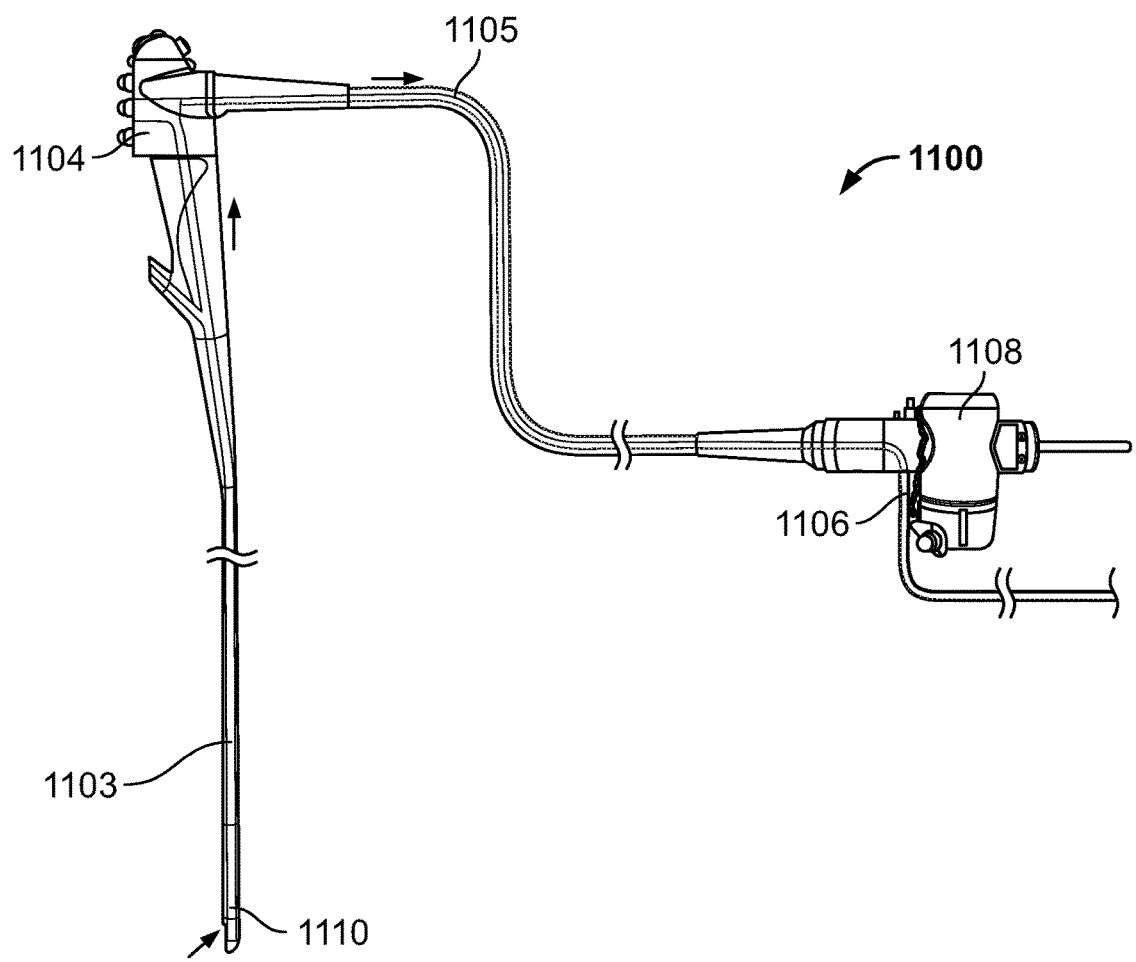
FIG. 11B is a cross-sectional illustration of an endoscope depicting the pathway of steam during a sterilization procedure, in accordance with another embodiment of the present specification.
Figure 11C:
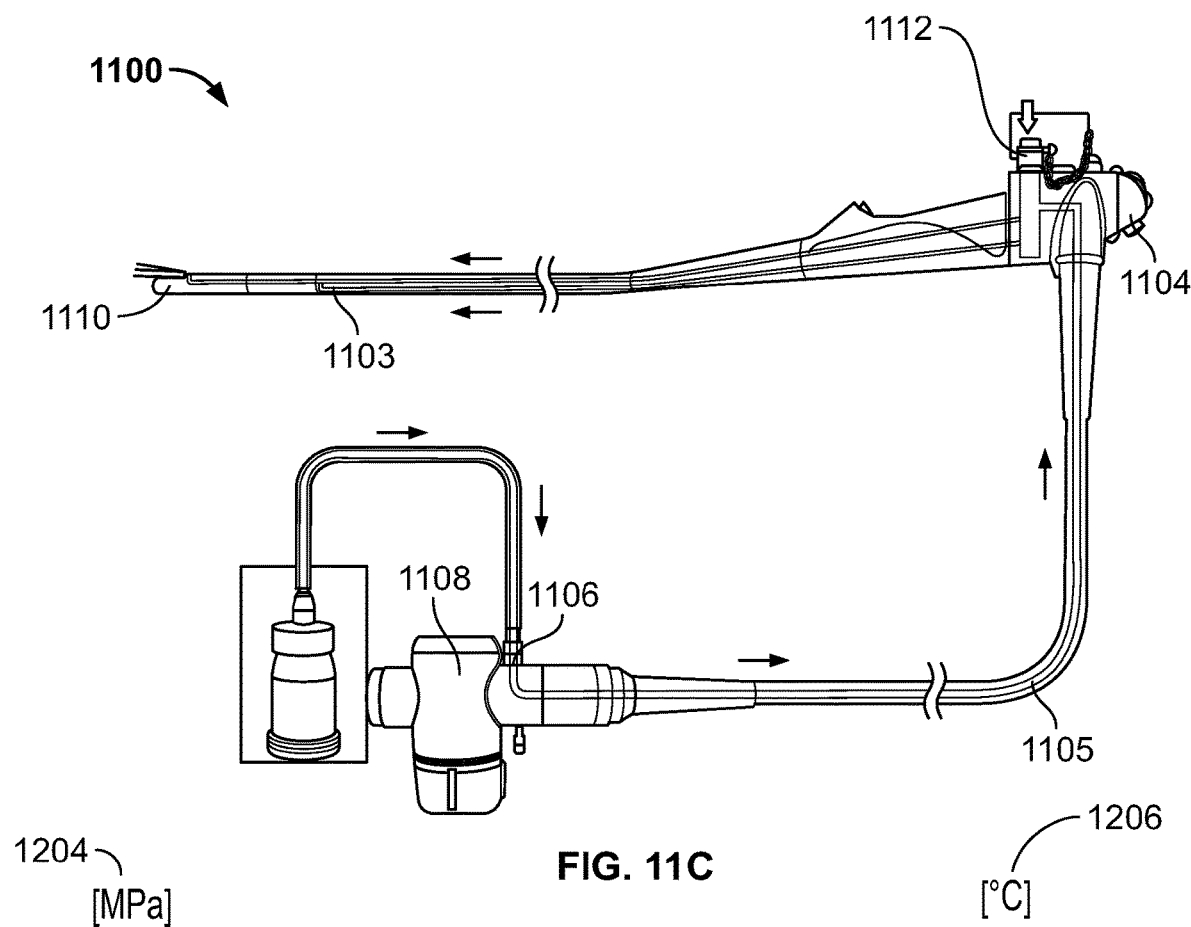
FIG. 11C is a cross-sectional illustration of an endoscope depicting the pathway of steam during a sterilization procedure, in accordance with yet another embodiment of the present specification.

FIGS. 11A, 11B, and 11C are cross-sectional illustrations of endoscopes 1100 depicting the pathway of steam 1105 during a sterilization procedure, in accordance with some embodiments of the present specification. As shown in FIG. 11A, a steam source may be connected to a port 1102 on a handle 1104 of the endoscope 1100 and by sealing off the remaining ports of the endoscope, steam 1105 is caused to circulate through the endoscope's channel for a desired period of time for sterilizing the channels. Once the sterilization process is complete, the steam may leave the channels via a port 1106 provided on a connector 1108 of the endoscope.

As shown in FIG. 11B, a steam source may be connected to an opening in a tip 1110 of the insertion tube 1103 of the endoscope 1100 and by sealing off the remaining ports of the endoscope, steam 1105 is caused to circulate through the endoscope's channel for a desired period of time for sterilizing the channels. Once the sterilization process is complete the steam may leave the channels via a port 1106 provided on a connector 1108 of the endoscope.

As shown in FIG. 11C water, steam, $H_2O_2$, $H_2O_2$ plasma gas, or any other sterilization agent know in the art 1105 enters the endoscope channels via a port 1106 provided on a connector 1108 of the endoscope 1100 and circulates through all of the scope's channels exiting at an opening in the tip 1110 of the insertion tube 1103. In an embodiment, any suitable disinfectant for disinfecting the endoscope channels may also be pushed in via port 1106. The ports on the handle 1104 are sealed off by using a compression fitting 1112.

Figure 12:
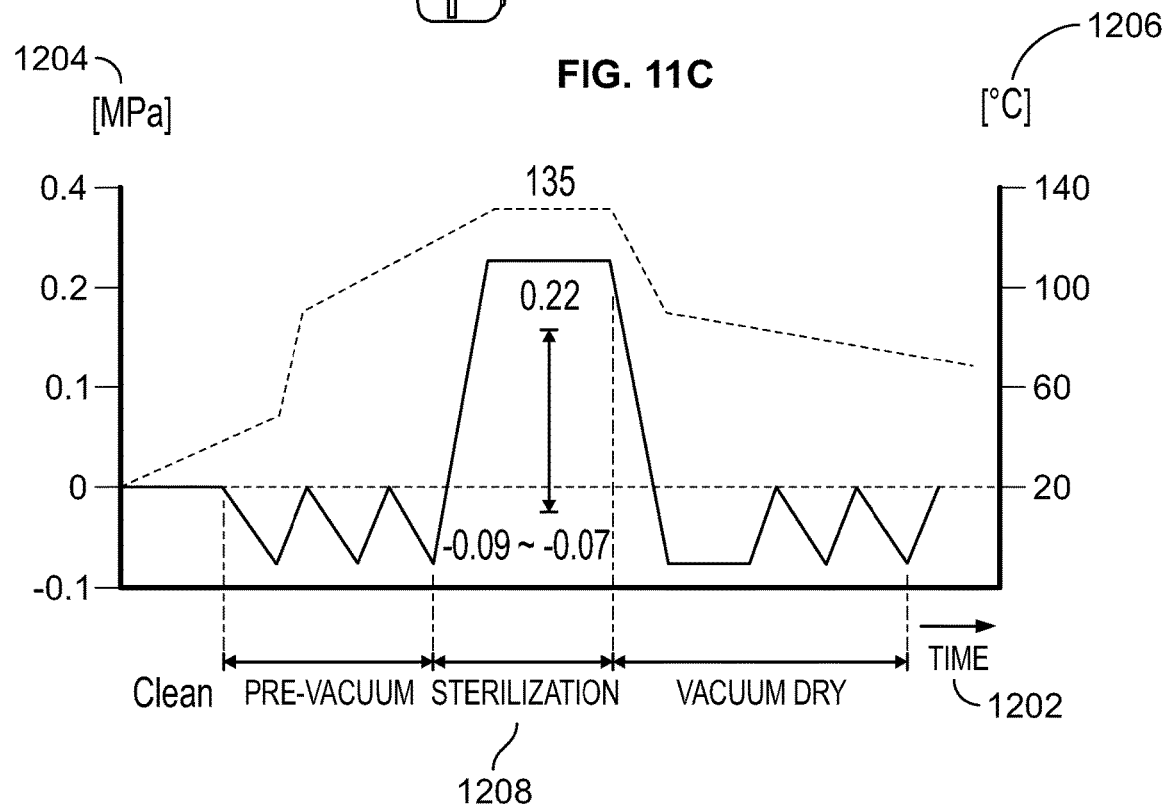
FIG. 12 is a graph illustrating the relationship between time, pressure, and temperature for various stages of sterilizing an endoscope using steam, in accordance with some embodiments of the present specification.

FIG. 12 is a graph illustrating the relationship between time 1202, pressure 1204, and temperature 1206 for various stages of sterilizing an endoscope using steam, in accordance with some embodiments of the present specification. Sterilization 1208 occurs when the temperature is maintained over 100° C. and pressure is maintained over 0.2 MPa for a specific amount of time. In some embodiments, said amount of time ranges from 3 minutes to 60 minutes.

Figure 13A:
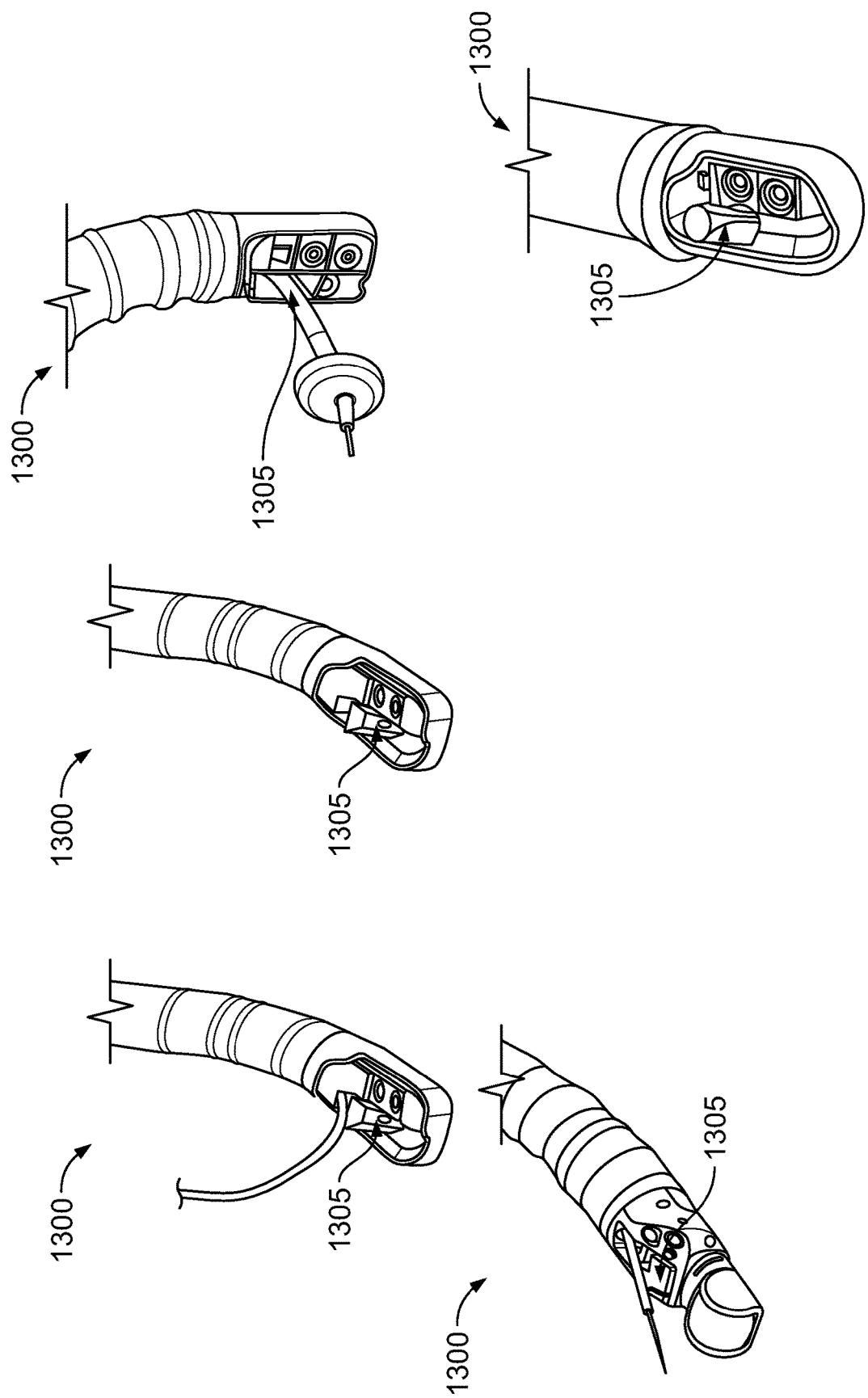
FIG. 13A is an illustration of a distal end of an endoscope used in ERCP procedures, depicting an elevator channel.

FIG. 13A is an illustration of a distal end of an endoscope used in Endoscopic Retrograde Cholangiopancreatography (ERCP) procedures. The Endoscope also known in the art as duodenoscope comprises a wire channel also known as an elevator channel 1305 for insertion of medical instruments within a patient's body cavity. In some available models, The ERCP endoscope's elevator 1305 wire channel is 'sealed' to prevent its contamination with such bacteria and superbugs such as carbapenem-resistant Enterobacteriaceae, or CRE. The 'sealed' elevator wire channel 1305, or the 'sealed' distal hood or case at the ERCP endoscope's distal tip, can retain debris and infectious CRE (inaccessible to the disinfectant and cleaning brush) that are transmitted to patients during subsequent ERCP procedures. In general, high-level disinfectants rapidly kill vegetative bacteria, such as CRE, if the disinfectant is not precluded from contacting the organism by the reusable instrument's physical design. However, in most cases conventional means of disinfecting and cleaning the elevator channel 1305 prove to be inefficient and ineffective.

Figure 13B:
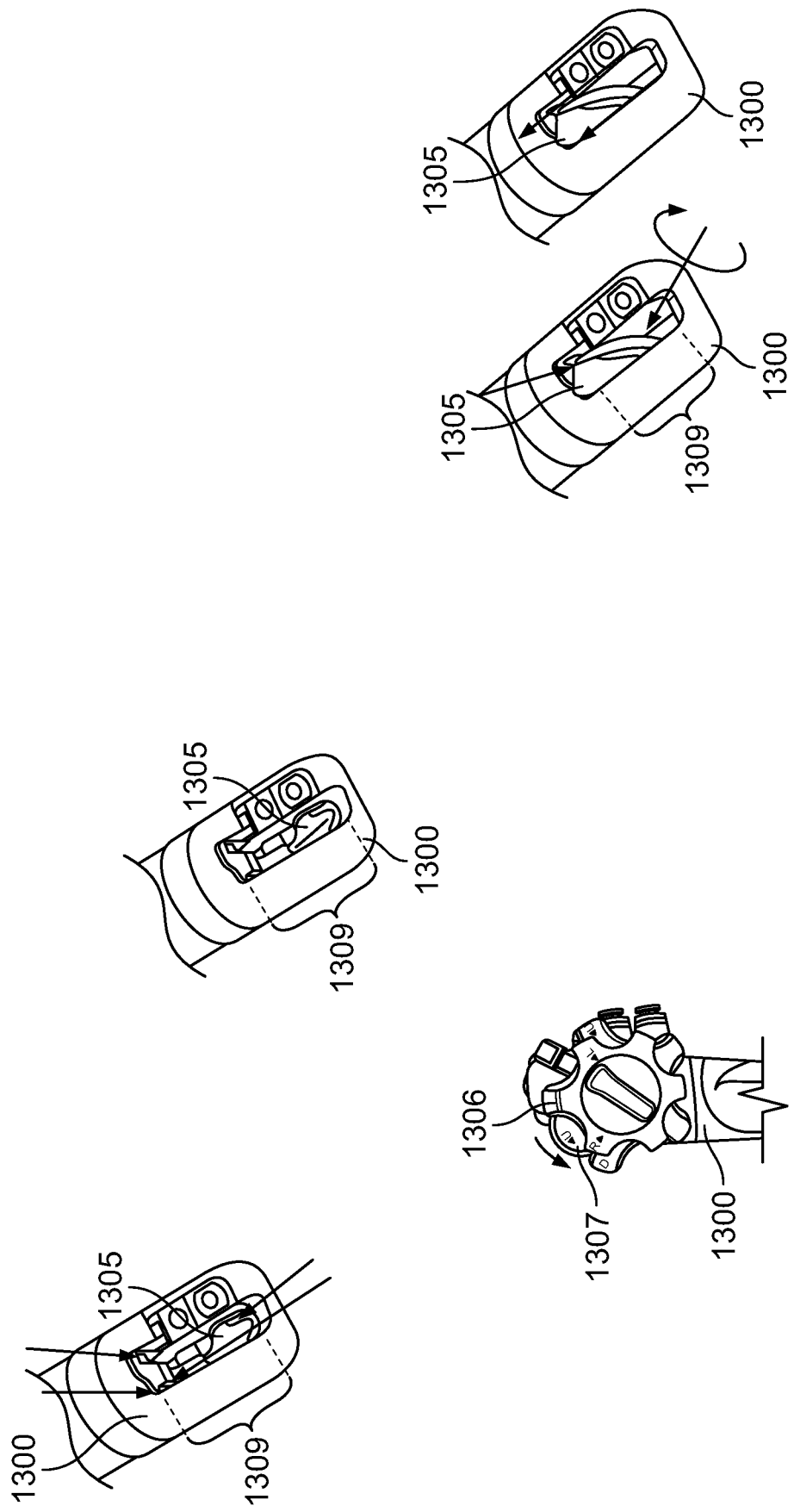
FIG. 13B is an illustration of movement of an elevator at the distal tip of an endoscope to allow for complete sterilization, in accordance with one embodiment of the present specification.

In various embodiments, the elevator channel may be efficiently and thoroughly cleaned and sterilized by the passage of steam through the channel. FIG. 13B is an illustration of movement of an elevator 1305 at the distal tip of an endoscope 1300 to allow for complete sterilization, in accordance with one embodiment of the present specification. The elevator 1305 may be moved manually, by using a lever 1307 on the handle 1306 of the endoscope 1300, or by a mechanism included in the sterilization system and configured to move the elevator 1305 during sterilization. Movement of the elevator 1305 during sterilization allows steam access to an elevator recess 1309 during sterilization for complete sterilizing.

Figure 14A:
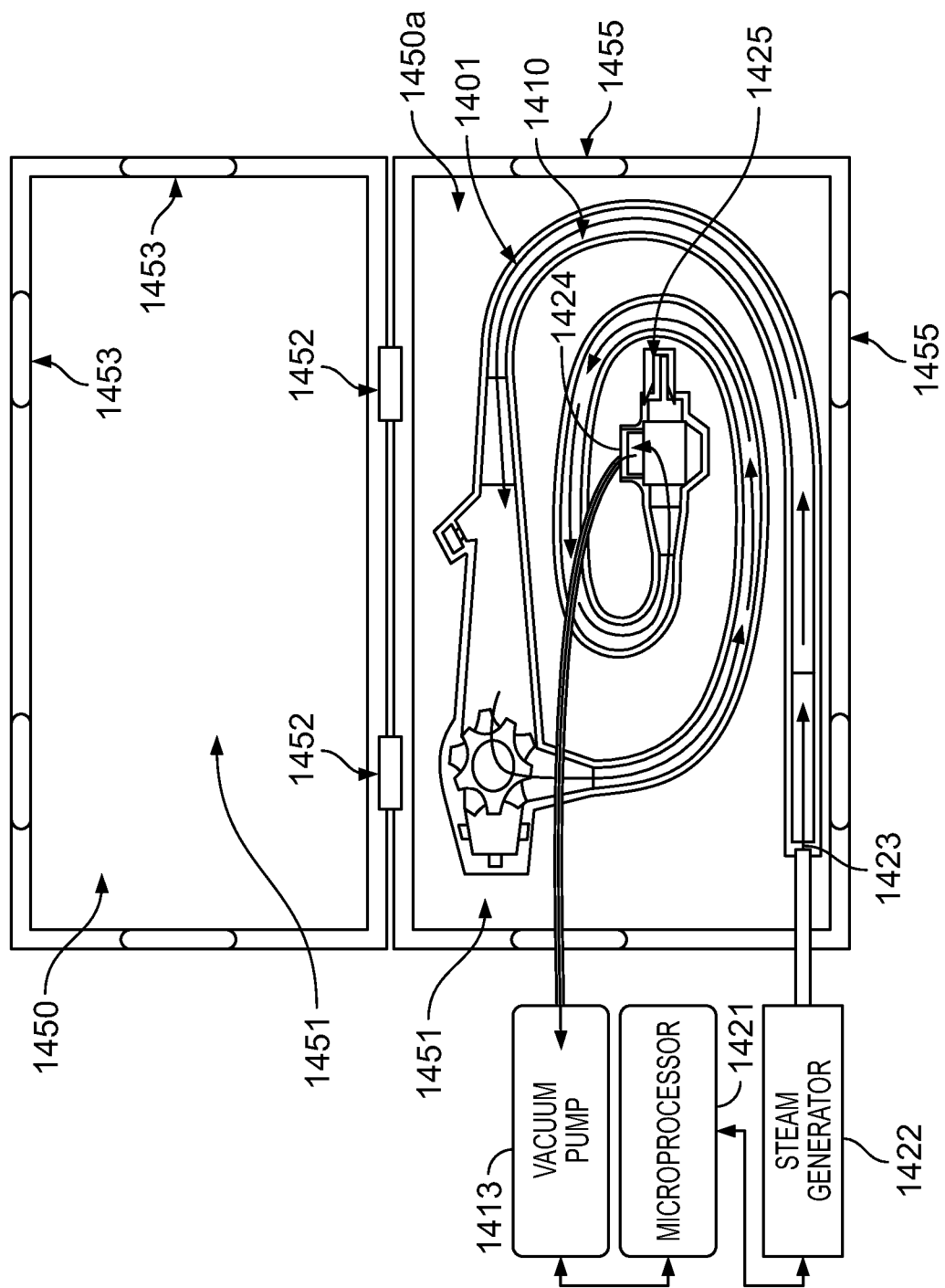
FIG. 14A is an illustration of a thermally insulated casing for use with steam sterilization of an endoscope, in accordance with one embodiment of the present specification.

FIG. 14A is an illustration of a thermally insulated casing or sterilization chamber 1450 for use with steam sterilization of an endoscope 1400, in accordance with one embodiment of the present specification. The chamber 1450 comprises two halves connected by hinges 1452 wherein each half is lined on the inside with a thermally insulating liner 1451. A first half 1450a of the chamber 1450 opens to receive an endoscope 1400 in an endoscope well 1401 for sterilization. Male clasps 1453 connect with female clasps 1455 to keep the chamber 1450 securely closed during sterilization. A steam generator 1422 introduces steam, via a compression fitting 1423, into the endoscope 1400. The steam travels along a pathway 1410 in the endoscope channels to sterilize the endoscope 1400. A vacuum pump 1413 is attached by a pressure resistant fitting 1424 to the endoscope to remove steam or any trapped air from the endoscope channels via suction. A pressure resistant fitting 1425 prevents the steam from escaping the channels of the endoscope thereby protecting the electronic connections of the endoscope 1400 from high pressure steam. A microprocessor 1421 controls both the steam generator 1422 and the vacuum pump 1413 and causes the steam to reach a therapeutic temperature and pressure.

Figure 14B:
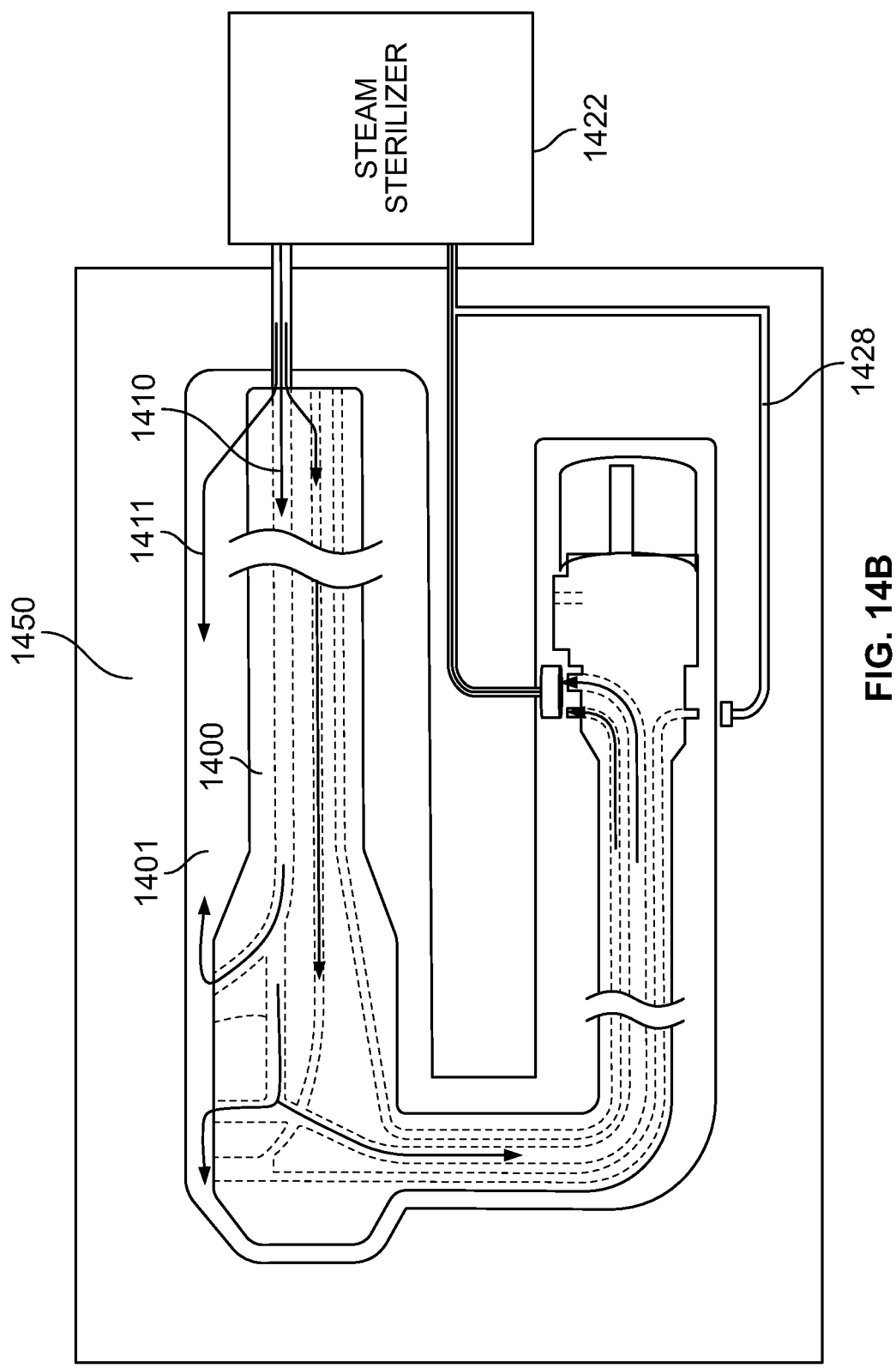
FIG. 14B is an illustration of a thermally insulated casing for use with steam sterilization of an endoscope, in accordance with another embodiment of the present specification.

FIG. 14B is an illustration of a thermally insulated casing or sterilization chamber 1450 for use with steam sterilization of an endoscope 1400, in accordance with another embodiment of the present specification. A steam generator 1422 delivers steam into a well 1401 in the chamber 1450 holding the endoscope. The steam is free to follow pathways 1410 in the channels of the endoscope and pathways 1411 about the exterior of the endoscope 1400, existing in a space between the well 1401 of the chamber 1450 and the endoscope 1400. Once the sterilization process is complete, the steam is suctioned out via tubing 1428 connected to a vacuum pump (not shown in FIG. 14B).

Figure 14C:
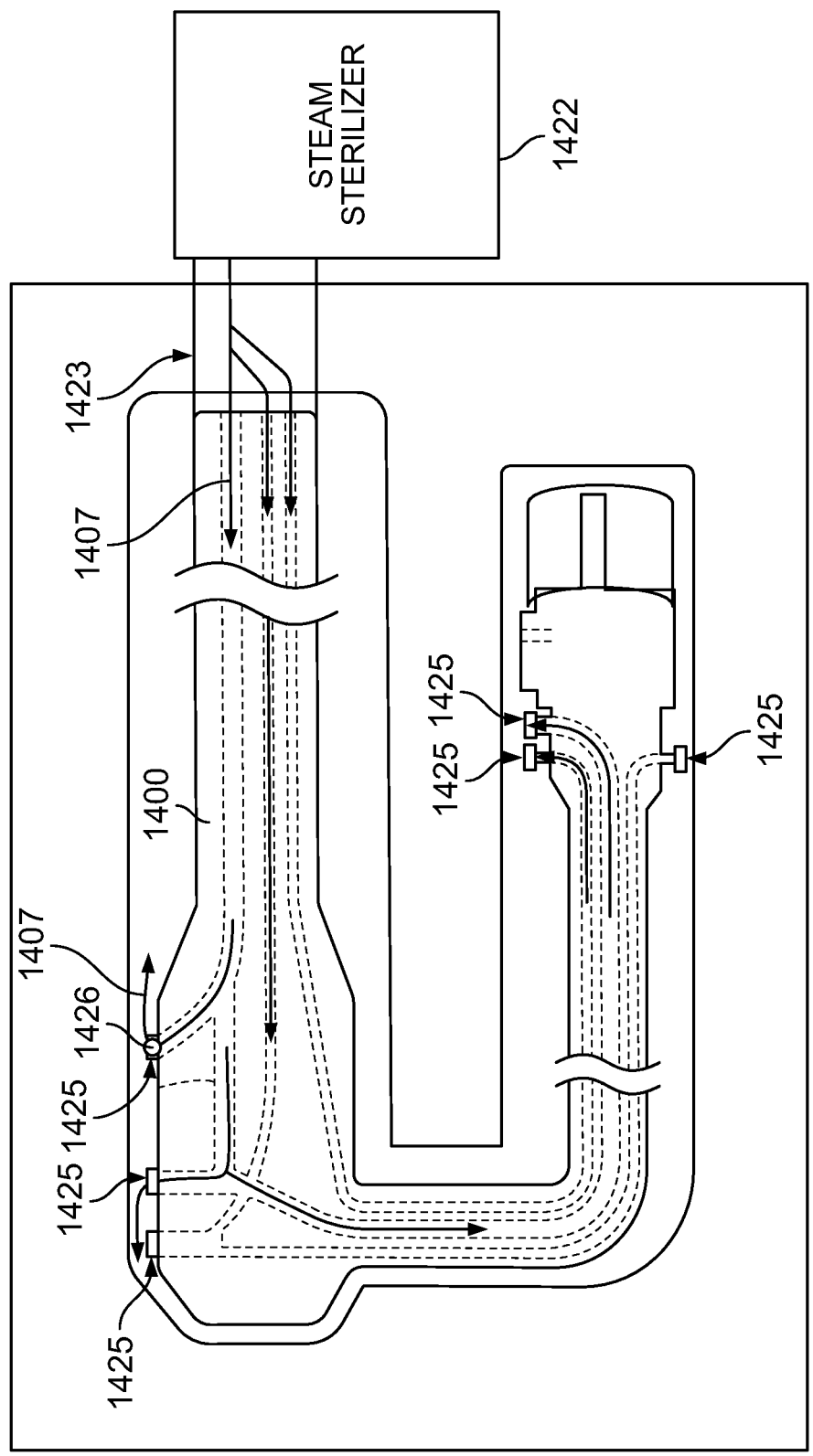
FIG. 14C is an illustration of a thermally insulated casing for use with steam sterilization of an endoscope, in accordance with yet another embodiment of the present specification.

FIG. 14C is an illustration of a thermally insulated casing 1450 for use in steam sterilization of an endoscope 1400, in accordance with yet another embodiment of the present specification. Steam 1407 from a steam generator 1422 is forced through the scope tip through a pressure resistant compression fitting 1423. Additional pressure resistant fittings 1425 are applied to all the remaining openings of the endoscope 1400. One or all of the pressure resistance fittings have a pressure relief valve 1426 which opens at a pressure lower than the desired pressure for sterilization. As the steam 1407 is forced through the endoscope channels, the pressure builds up in the channels and, as it approaches the relief pressure, the valve 1426 opens, allowing the steam to escape and then circulate around the endoscope 1400, sterilizing the outside of the endoscope 1400.

Figure 15:
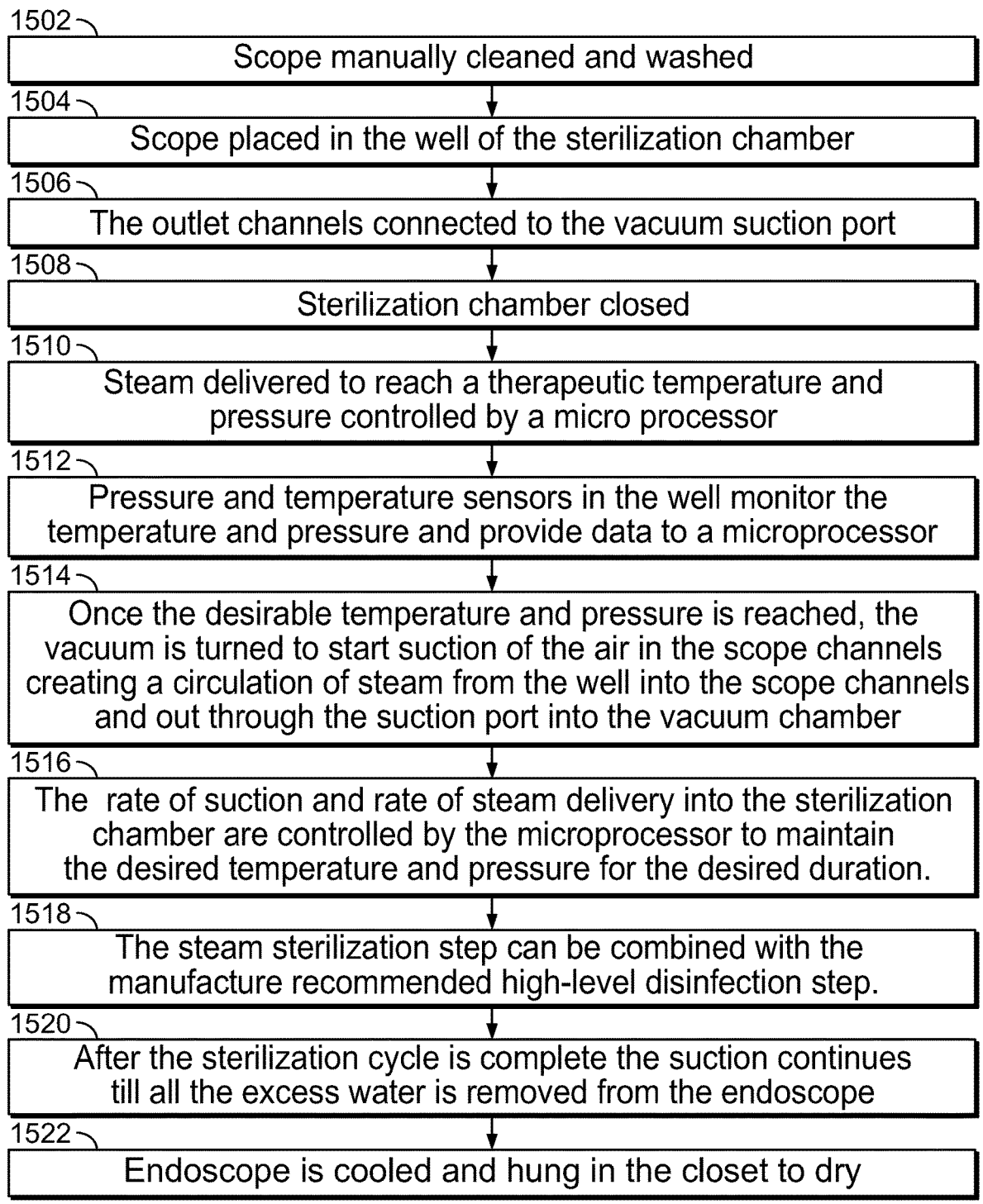
FIG. 15 is a flowchart listing the steps involved in a method of using a thermally insulated casing and steam to sterilize an endoscope, in accordance with one embodiment of the present specification.

FIG. 15 is a flowchart listing the steps involved in a method of using a thermally insulated casing, or sterilization chamber, and steam to sterilize an endoscope, in accordance with one embodiment of the present specification. At step 1502, the endoscope is manually cleaned and washed. The endoscope is placed in the well of the sterilization chamber at step 1504. Then, at step 1506, the outlet channels of the endoscope are connected to a vacuum suction port. The sterilization chamber is closed at step 1508. Steam is delivered to reach a therapeutic temperature and pressure controlled by a microprocessor at step 1510. At step 1512, pressure and temperature sensors in the well monitor the temperature and pressure and provide data to the microprocessor. Once the desirable temperature and pressure is reached, the vacuum is turned on to start suction of the air in the endoscope channels at step 1514, creating a circulation of steam from the well into the endoscope channels and out through the suction port into the vacuum chamber, thereby releasing the pressure. At step 1516, the rate of suction and rate of steam delivery into the sterilization chamber are controlled by the microprocessor to maintain the desired temperature and pressure for the desired duration. Optionally, at step 1518, the steam sterilization is combined with the manufacturer recommended high-level disinfection. After the sterilization cycle is complete, the suction continues until all of the excess water is removed from the endoscope at step 1520. Then, at step 1522, the endoscope is cooled and hung in the closet to dry.

Figure 16:
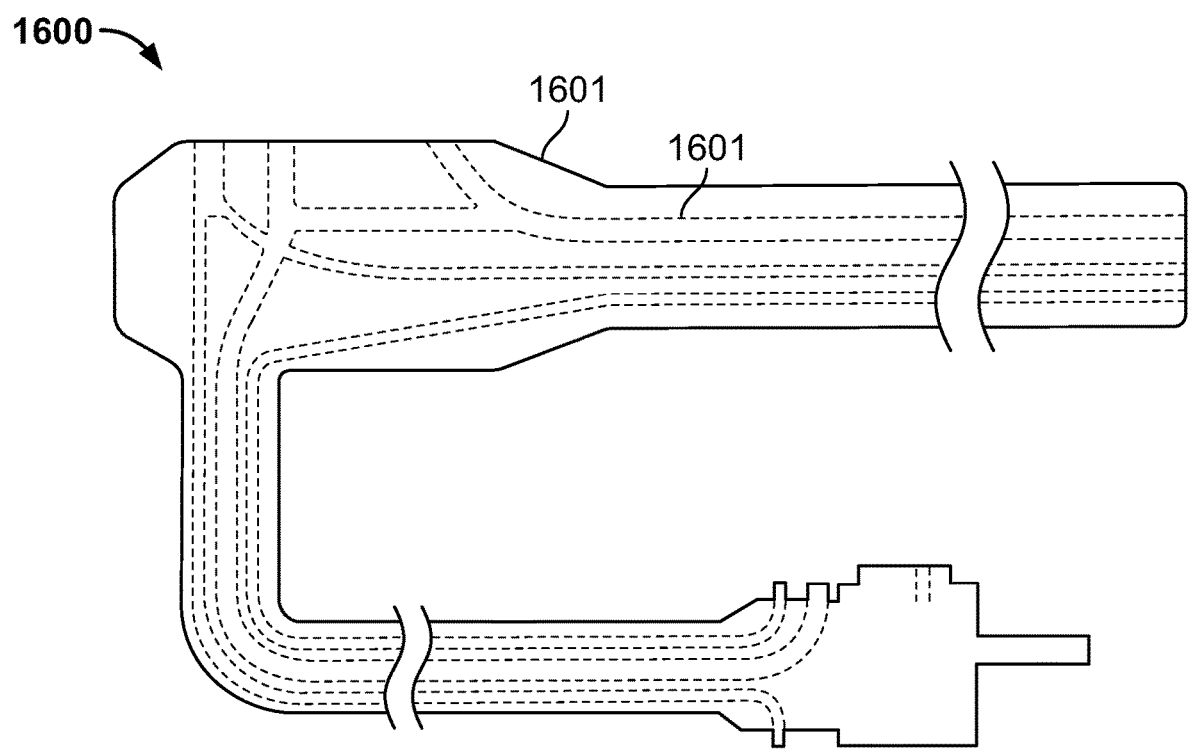
FIG. 16 is an illustration of an endoscope capable of withstanding high temperatures involved with steam sterilization, in accordance with one embodiment of the present specification.

FIG. 16 is an illustration of an endoscope 1600 capable of withstanding high temperatures involved with steam sterilization, in accordance with one embodiment of the present specification. All the components of the endoscope 1600 can withstand a temperature greater than 100° C. and preferably greater than 150° C. In an embodiment, the skin 1601 of the endoscope, including the lining of the channels, is made with silicone, Teflon®, polyethylene terephthalate (PET), polypropylene, polybenzimidazole, or a thermoplastic polymer or any other material that can withstand temperatures greater than 100° C. and preferably greater than 150° C. The electronic components are also designed to withstand a temperature greater than 100° C. and preferably greater than 150° C.

In some embodiments of the present specification, a sterilization system is provided wherein instead of the use of pressurized compression fittings as described in the above embodiments, separate pressurized chambers are used. The endoscope is placed in a casing in which separate chambers can be created by using separators which force the disinfecting agent from one chamber to the other through the endoscope's channels based on pressure differences between the various chambers. The separators are automated for opening and closing as an area of contact with the outside of the endoscope is occluded from contact with the sterilizing agent. The separators are then removed before the outside of the endoscope goes through sterilization process.

Figure 17A:
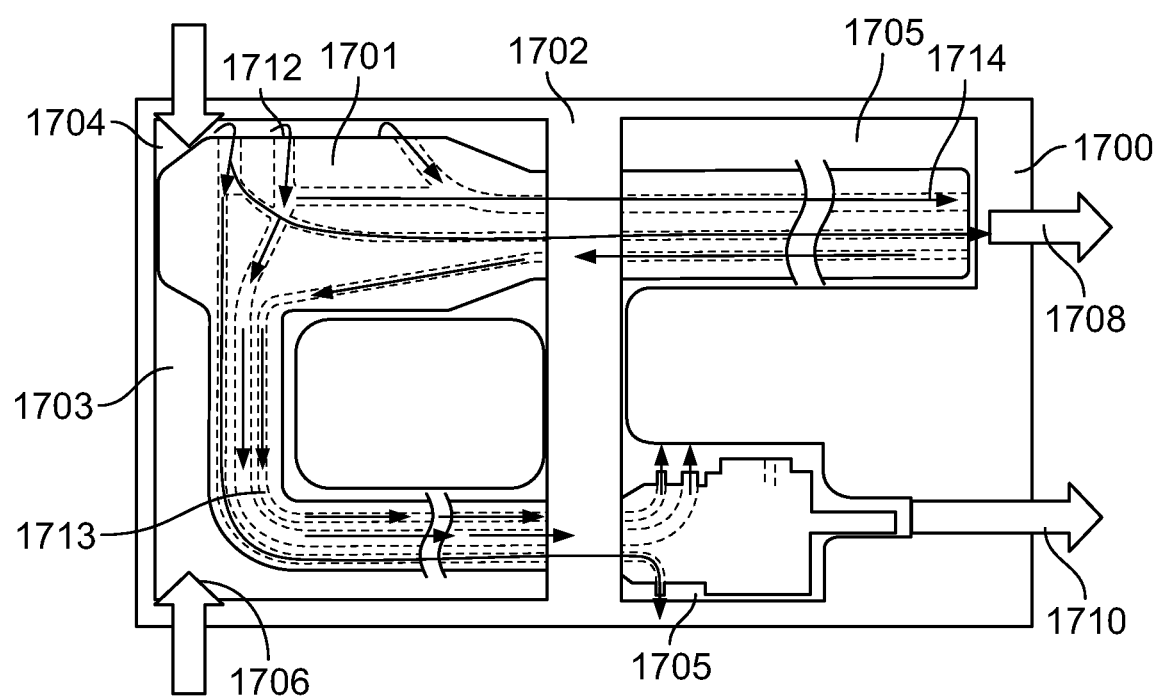
FIG. 17A is an illustration of a thermally insulated casing or sterilization chamber subdivided into one or more chambers, in accordance with one embodiment of the present specification.

FIG. 17A is an illustration of a thermally insulated casing 1700 or sterilization chamber or apparatus subdivided into two or more chambers 1703, 1705, in accordance with one embodiment of the present specification. As shown, casing 1700 is divided into two chambers by means of separating component or separator 1702. Each of the channel openings or ports of an endoscope 1701 placed in the casing 1700 for the purpose of sterilization occupies one or more of the chambers 1703, 1705. In embodiments, one or more of the chambers are pressurized with steam which enters chamber 1703 of casing 1700 through first openings 1704, 1706. The steam is pushed through one or more of the first ports 1712 of the endoscope to pass through endoscope channels 1713 and out through second ports 1714. The steam then passes out of one or more of the second openings 1708, 1710 in chamber 1705, thereby circulating the steam in and around the endoscope due to the pressure difference created by the separator 1702 between the chambers 1703, 1705. In some embodiments, the pressure is greater in chamber 1703 relative to the pressure in chamber 1705 to cause the sterilizing agent to travel from chamber 1703, through the endoscope channels 1713, and out through chamber 1705. In embodiments, temperature sensors are provided in one or more of the chambers to monitor the temperature in that chamber. Further, optional pressure sensors may also be provided in the chambers to monitor the pressure in that chamber. There is an optional outlet provided in one or more of the chambers to allow the air or vapor to exit the chamber. The opening 1704 and 1706 and the outlets 1708 and 1710 are optionally controlled by a microprocessor to control the delivery of sterilizing agent and maintain adequate contact time at the adequate parameters.

Figure 17B:
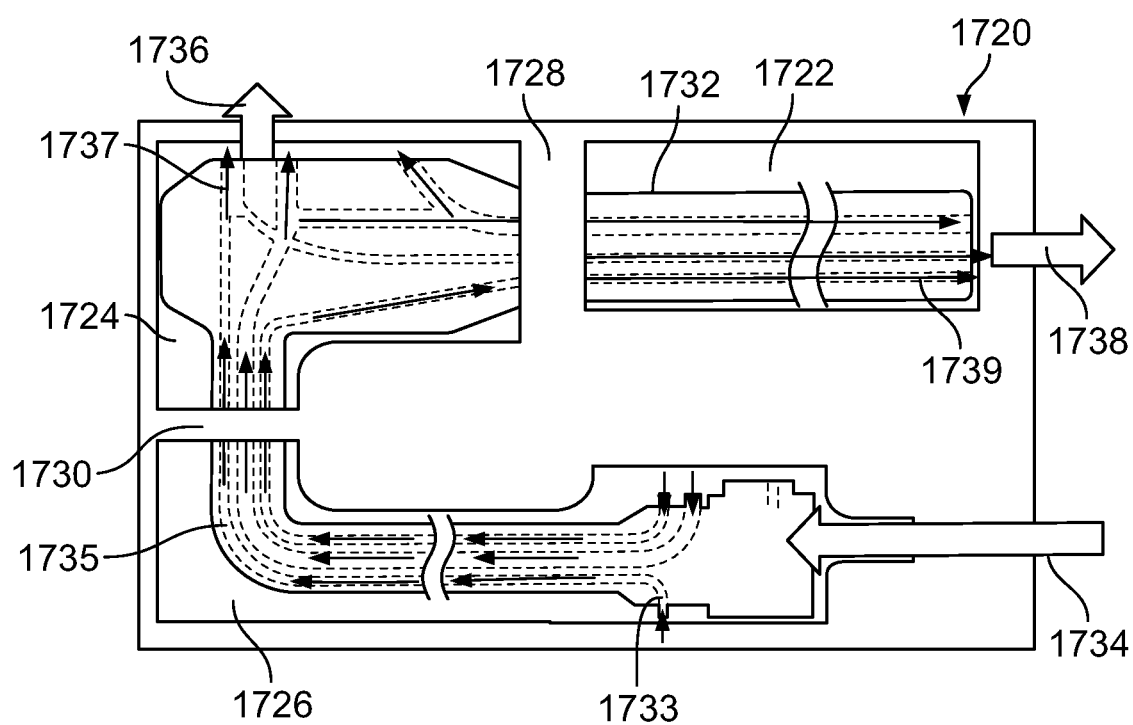
FIG. 17B is an illustration of a thermally insulated casing or sterilization chamber subdivided into one or more chambers, in accordance with another embodiment of the present specification.

FIG. 17B is an illustration of a thermally insulated casing 1720 or sterilization chamber subdivided into two or more chambers, in accordance with another embodiment of the present specification. As shown, casing 1720 is divided into three chambers 1722, 1724 and 1726 by using separating components or separators 1728 and 1730. In an embodiment, the separators 1728, 1730 are automated and may be removed during the sterilization process, allowing the vapor/sterilizing agent flowing through the chambers 1722, 1724 and 1726 to mix to create a uniform sterilization temperature and pressure on the outside of the endoscope 1732. The sterilizing agent is pushed in via a channel 1734 of the casing 1720 and into ports 1733 of the endoscope 1732 where it circulates through the endoscope channels 1735 and exits, due to the pressure difference between chambers 1722, 1724, 1726 out of ports 1737 or ports 1739 of the endoscope 1732 and out of channels 1736 or 1738 of the casing 1720. In some embodiments, the pressure is greater in chamber 1726 relative to the pressure in chambers 1724 and 1726 to cause the sterilizing agent to travel from chamber 1726, through the endoscope channels 1735, and out through chambers 1724, 1726.

In various embodiments, methods for agitating the sterilizing or disinfecting agents in each of the chambers is provided to improve the sterilizing or disinfecting process by dislodging organic material from the surface of the endoscope. The method of agitation may include one of mechanical agitation or sound waves.

Figure 18:
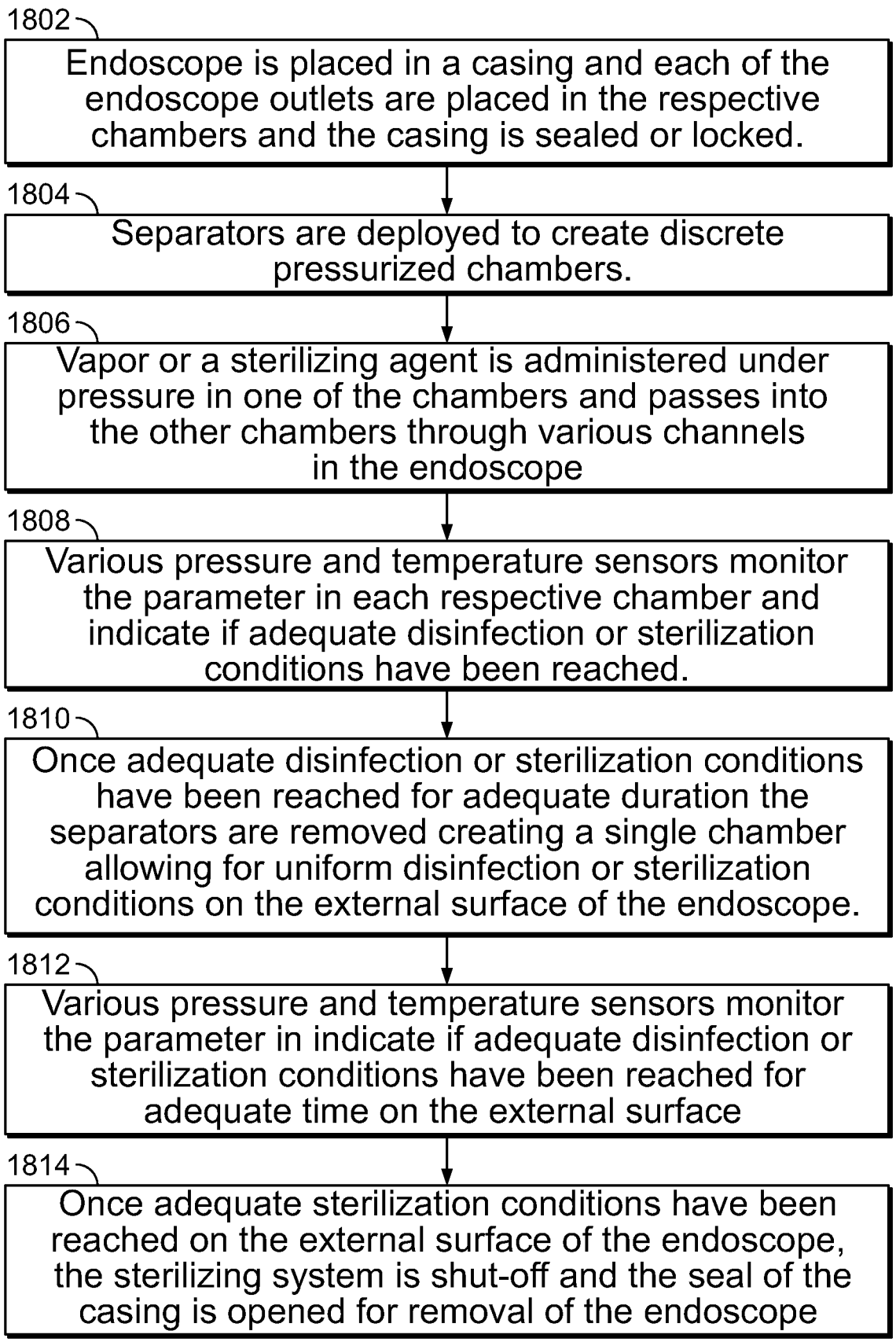
FIG. 18 is a flowchart illustrating the steps of sterilizing an endoscope by using pressurized chambers, in accordance with an embodiment of the present specification.

FIG. 18 is a flowchart illustrating the steps of sterilizing an endoscope by using pressurized chambers, in accordance with an embodiment of the present specification. At step 1802 the endoscope is placed in a casing comprising two or more chambers created by the use of separators within the casing, and each of the endoscope's ports or outlets are placed in the respective chambers and the casing is sealed or locked. At step 1804, the separators are deployed to pressurize the discreet chambers. At step 1806, vapor or a sterilizing agent is administered under pressure in one of the chambers and passed into the other chambers through various channels in the endoscope. At step 1808, various pressure and temperature sensors provided in the chambers monitor predefined parameters in each respective chamber and indicate if adequate disinfection or sterilization conditions have been reached. At step 1810, once adequate disinfection or sterilization conditions have been reached for adequate duration (which may range from 3 minutes to 60 minutes), the separators are removed creating a single chamber allowing for uniform disinfection or sterilization conditions on the external surface of the endoscope. At step 1812, the various pressure and temperature sensors monitor the predefined parameters to determine if adequate disinfection or sterilization conditions have been reached for adequate time on the external surface. Next, at step 1814, once adequate disinfection or sterilization conditions have been reached for adequate time on the external surface of the endoscope, the sterilizing system is shut-off and the lock or seal of the casing is opened for removal of the endoscope.

The above examples are merely illustrative of the many applications of the system of the present invention. Although only a few embodiments of the present invention have been described herein, it should be understood that the present invention might be embodied in many other specific forms without departing from the spirit or scope of the invention. Therefore, the present examples and embodiments are to be considered as illustrative and not restrictive, and the invention may be modified within the scope of the appended claims.

We claim:

1. An apparatus for disinfecting or sterilizing an endoscope, comprising:
    at least one pressure resistant compression fitting designed to be operably attached to one opening of an endoscope;
    a disinfecting or sterilizing agent generator capable of delivering a disinfecting or sterilizing agent and attached to said at least one pressure resistant compression fitting via a length of tubing;

at least one pressure resistant vacuum suction fitting designed to be operably attached to another opening of an endoscope at one end and attached to a vacuum suction at the other end; and a microprocessor operably attached to the disinfecting or sterilizing agent generator and vacuum pump to control the rate of delivery of disinfecting or sterilizing agent and rate of suction.

2. The apparatus of claim 1, further comprising additional disinfecting or sterilizing agent delivery ports for delivery of disinfecting or sterilizing agent into one of the other openings of the endoscope.

3. The apparatus of claim 1, further comprising additional suction ports for suction of disinfecting or sterilizing agent from one of the other openings of the endoscope.

4. The apparatus of claim 1, further comprising sensors to measure at least one of a plurality of parameters of the disinfecting or sterilizing agent and input measured data into the microprocessor to control the delivery of disinfecting or sterilizing agent or rate of suction or both.

5. The apparatus of claim 1, wherein said microprocessor further comprises a user interface to input operational data or to monitor the progress of disinfection or sterilization.

6. The apparatus of claim 1 wherein the disinfecting or sterilizing agent is superheated steam and the disinfecting or sterilizing agent generator comprises a steam generator.

7. The apparatus of claim 1 wherein the disinfecting or sterilizing agent is at least one of hydrogen peroxide or ionized plasma gel.

8. An apparatus for disinfecting or sterilizing an endoscope, comprising:

a thermally insulating casing with at least one pressure resistant compression fitting designed to be operably attached to one opening of an endoscope;

adisinfecting or sterilizing agent generator capable of delivering a disinfecting or sterilizing agent and attached to said pressure resistant compressing fitting;

at least one vacuum suction port operably attached to the casing at one end and attached to a vacuum suction at the other end to provide suction; and a microprocessor operably attached to the disinfecting or sterilizing agent generator and vacuum pump to control the rate of delivery of disinfecting or sterilizing agent and rate of suction.

9. The apparatus of claim 8, further comprising additional disinfecting or sterilizing agent delivery ports for delivery of disinfecting or sterilizing agent into one of the other openings of the endoscope and additional suction ports for the suction of disinfecting or sterilizing agent from one of the other openings of the endoscope.

10. The apparatus of claim 8, further comprising at least one sensor to measure any one of a plurality of parameters of the disinfecting or sterilizing agent and input measured data into the microprocessor to control the delivery of disinfecting or sterilizing agent or rate of suction or both.

11. The apparatus of claim 8, wherein said microprocessor includes a user interface to input operational data or to monitor the progress of disinfection or sterilization.

12. The apparatus of claim 8 wherein the disinfecting or sterilizing agent is superheated steam and the disinfecting or sterilizing agent generator comprises a steam generator.

13. The apparatus of claim 8 wherein the disinfecting or sterilizing agent is at least one of hydrogen peroxide or ionized plasma gel.

14. An apparatus for disinfecting or sterilizing an endoscope, comprising:

at least two chambers separated by a separating component;

a space for placing an endoscope wherein a first portion of said endoscope comprising at least one first endoscope port is positioned in a first chamber of said at least two chambers and a second portion of said endoscope comprising at least one second endoscope port is positioned in a second chamber of said at least two chambers;

at least one first opening providing fluid communication between said first chamber and an outside area of said apparatus; and at least one second opening providing fluid communication between said second chamber and an outside area of said apparatus;

wherein a disinfecting or sterilizing agent is introduced under pressure through said first or second opening and into said first or second chamber and wherein a pressure difference between said first chamber and said second chamber causes said disinfecting or sterilizing agent to enter said endoscope through said first endoscope port or said second endoscope port, pass through one or more endoscope channels of said endoscope, exit said endoscope through said first endoscope port or said second endoscope port not comprising the endoscope port through which said disinfecting or sterilizing agent entered said endoscope, and exit said apparatus through said first or second opening not comprising the opening through which the disinfecting or sterilizing agent entered said apparatus.

15. The apparatus of claim 14 wherein the disinfecting or sterilizing agent is superheated steam and wherein the apparatus further comprises a steam generator for introducing the superheated steam through said first or second opening.

16. The apparatus of claim 14 wherein the disinfecting or sterilizing agent is at least one of hydrogen peroxide or ionized plasma gel.

17. The apparatus of claim 14, further comprising additional endoscope ports positioned in the first chamber, wherein the disinfecting or sterilizing agent is configured to enter or exit the endoscope through the additional endoscope ports.

18. The apparatus of claim 14, further comprising additional endoscope ports positioned in the second chamber, wherein the disinfecting or sterilizing agent is configured to enter or exit the endoscope through the additional endoscope ports.

19. The apparatus of claim 14, further comprising sensors to measure at least one of a plurality of parameters of the disinfecting or sterilizing agent and input measured data into the microprocessor to control the delivery of disinfecting or sterilizing agent or rate of suction or both.

20. The apparatus of claim 14, wherein said microprocessor further comprises a user interface to input operational data or to monitor the progress of disinfection or sterilization.

* * * * *